(12) United States Patent
Sidorsky et al.

(10) Patent No.: US 9,176,026 B2
(45) Date of Patent: Nov. 3, 2015

(54) DEVICE FOR THE COLLECTION, REFINEMENT, AND ADMINISTRATION OF GASTROINTESTINAL MICROFLORA

(71) Applicant: PureFlora, Inc., San Francisco, CA (US)

(72) Inventors: Tivon I. Sidorsky, San Francisco, CA (US); Brian S. Placek, Menlo Park, CA (US); Alexander J. Engler, Weston, MA (US); William H. Hart, Kenilworth, IL (US); Peter W. Ankeny, Wayzata, MN (US); Misha N. Sidorsky, Somerville, MA (US)

(73) Assignee: PUREFLORA, INC., San Francisco, CA (US)

( * ) Notice: Subject to any disclaimer, the term of this patent is extended or adjusted under 35 U.S.C. 154(b) by 0 days.

(21) Appl. No.: 13/715,178

(22) Filed: Dec. 14, 2012

(65) Prior Publication Data

US 2014/0017720 A1 Jan. 16, 2014

Related U.S. Application Data

(60) Provisional application No. 61/576,175, filed on Dec. 15, 2011, provisional application No. 61/563,642, filed on May 31, 2012.

(51) Int. Cl.
| | | |
|---|---|---|
| *C12Q 1/24* | (2006.01) | |
| *C12M 1/00* | (2006.01) | |
| *G01N 1/10* | (2006.01) | |
| *A61J 1/00* | (2006.01) | |
| *A61B 10/00* | (2006.01) | |

(52) U.S. Cl.
CPC .............. *G01N 1/10* (2013.01); *A61B 10/0038* (2013.01); *A61J 1/00* (2013.01); *A61B 10/0096* (2013.01)

(58) Field of Classification Search
CPC .................................. C12Q 1/24; C12M 1/00
See application file for complete search history.

(56) References Cited

U.S. PATENT DOCUMENTS

| | | | |
|---|---|---|---|
| 4,101,279 A | | 7/1978 | Aslam |
| 4,170,798 A | * | 10/1979 | Krumdieck .................. 4/319 |
| 4,849,173 A | | 7/1989 | Chang |
| 5,074,851 A | | 12/1991 | Plass et al. |
| 5,115,213 A | | 5/1992 | Eguchi |
| 5,116,754 A | * | 5/1992 | Fraser et al. ............. 435/252.1 |
| 5,380,647 A | | 1/1995 | Bahar |
| 5,556,544 A | | 9/1996 | Didier |
| 6,077,362 A | | 6/2000 | Reed |
| 6,351,857 B2 | | 3/2002 | Slaon, III et al. |
| 6,415,455 B1 | | 7/2002 | Slaon, III et al. |
| 6,630,585 B2 | | 10/2003 | Kojima |
| 8,241,591 B2 | | 8/2012 | Ribault et al. |
| 2005/0106753 A1 | | 5/2005 | Wu et al. |
| 2006/0122534 A1 | | 6/2006 | Matsumura et al. |
| 2008/0108961 A1 | | 5/2008 | Kik |
| 2008/0285378 A1 | | 11/2008 | Roggero |
| 2009/0258411 A1 | | 10/2009 | Petithory et al. |
| 2010/0331641 A1 | | 12/2010 | Bangera et al. |
| 2011/0020860 A1 | | 1/2011 | Greenwald |
| 2011/0189673 A1 | | 8/2011 | Tanigami et al. |

FOREIGN PATENT DOCUMENTS

| | | |
|---|---|---|
| EP | 2287331 A1 | 2/2011 |
| JP | 2005/296997 A | 11/1993 |
| WO | WO 2011/033310 A1 | 3/2011 |
| WO | WO 2011/094027 A1 | 8/2011 |
| WO | WO 2012/016287 A2 | 2/2012 |
| WO | WO 2012/122478 A1 | 9/2012 |
| WO | WO 2012/016287 A3 | 11/2012 |

OTHER PUBLICATIONS

"Squeezetest:The Gold Standard for fecal analysis". BGS Medical Products. (2010) pp. 1-2.*
BGS Medical Products. (The SqueezeTest: The Gold Standard for fecal analysis, 2000, pp. 1-2).*
Lovelady et al. (An improved Method for Preparation of Feces for Bomb Calorimetry. Clinical Chemistry (1970) 16: 253-254).*
Beckman-Coulter. HarvestLine System Liners Providing convenience and cost savings. 2001. www.beckmancoulter.com/harvestline.
Fecotainer. Patient friendly stool samping. Accessed Dec. 13, 2012. www.fecotainer.eu/en.
Sample preparation with BagSystem. Accessed Dec. 13, 2012. www.interscience.fr/lab-microbiology-analyses.
SEWARD. Stomacher 400 brochure. 2009. http://www.seward.co.uk/stomacher-400.htm.
International search report and written opinion dated Apr. 29, 2013 for PCT Application No. US2012/069921.

* cited by examiner

*Primary Examiner* — Karen Cochrane Carlson
*Assistant Examiner* — Natalie Moss
(74) *Attorney, Agent, or Firm* — Wilson Sonsini Goodrich & Rosati

(57) ABSTRACT

Methods and systems for isolating gastrointestinal microflora from stool collected from a donor are provided. Stool is collected from a donor in a container as the donor is defecating. A solvent is introduced into the container and the container sealed to place its contents in a sealed environment. Various agents can be added to achieve dissolving, colorizing, deodorizing, or for further therapies. The solvent and collected stool is homogenized into a mixture which is then filtered by a multi-stage filter system to create a solution containing microflora in the desired consistency. This solution can be dispensed via an enema tube or other delivery apparatus for infusion into a patient's gastrointestinal tract.

45 Claims, 42 Drawing Sheets

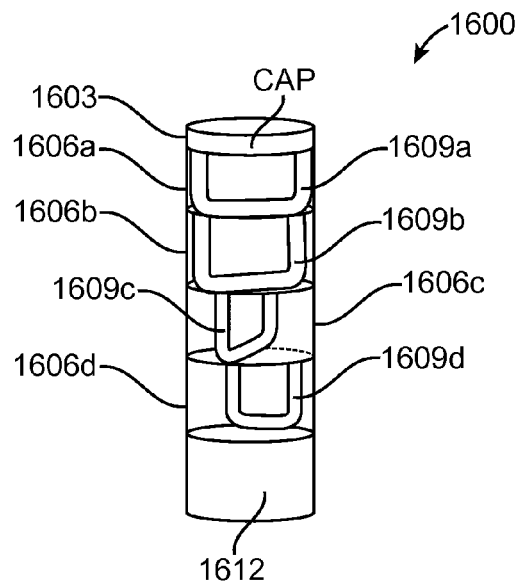
FIG. 16A
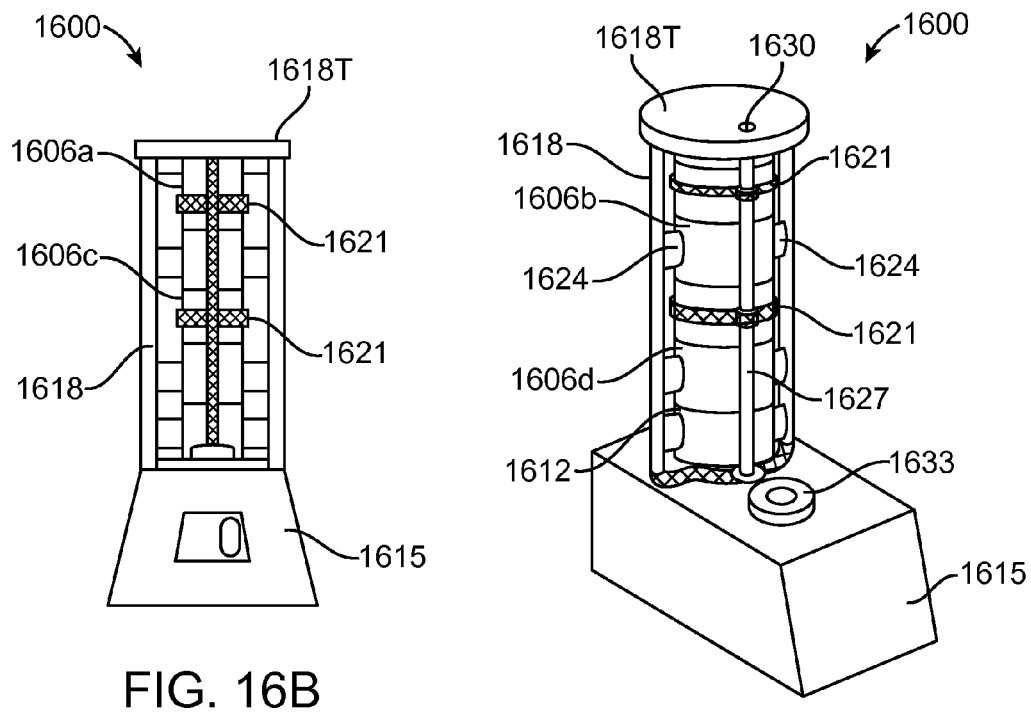
FIG. 16B
FIG. 16C

DEVICE FOR THE COLLECTION, REFINEMENT, AND ADMINISTRATION OF GASTROINTESTINAL MICROFLORA

CROSS-REFERENCE

This application claims the benefit of U.S. Provisional Application No. 61/576,175, filed Dec. 15, 2011, and U.S. Provisional Application No. 61/653,642, filed, May 31, 2012, which applications are incorporated herein by reference.

FIELD OF THE INVENTION

This invention relates to devices for the collection, processing, storage and transportation of donated stool and biotherapy involving collected gastrointestinal (GI) microflora for the treatment of a variety of morbidities in humans and animals.

BACKGROUND OF THE INVENTION

There is substantial and growing data suggesting that disruption of the normal, healthy gastrointestinal (GI) tract microbial environment (the GI microbiome), which consists of a wide variety of GI organisms (GI microflora), can play a critical role in the development of a wide variety of diseases affecting populations throughout the world. As such, there have been increasing efforts to develop strategies to restore imbalances in GI microflora. Such strategies include probiotics, and a process known as fecal microbiota transplantation (FMT) (also called "intestinal microflora transplantation", "fecal biotherapy", "fecal biotransplant", "fecal bacteriotherapy", "fecal flora reconstitution", "stool transplantation", or "fecal transplantation"), the latter of which seems to overcome all of the many disadvantages of the former. While, for purposes of clarity the term "FMT" or "fecal biotherapy" will be used for the remainder of this disclosure, the current inventors propose that this therapy be renamed "Gastrointestinal Floral Transplantation (GIFT)".

In sum, FMT involves the administration of a fully comprehensive composition or endogenous human GI microflora taken from a healthy (as determined by pre-treatment screening for stool and blood borne pathogens) donor's stool and delivered (transplanted) directly into the lower GI tract of an affected individual to reconstitute their disrupted microfloral environment. This strategy can overcome many of the limitations of oral probiotics, the commonly used, yet relatively ineffective strategy used to modify the GI microflora. First, unlike probiotics (the composition of which generally represent only 0.01% of roughly 100 trillion organisms in the normal GI microbiome), the microflora composition used in FMT approximates 100% of the normal GI microflora composition. Second, through various methods (most commonly colonoscopy, enema, or nasoenteric tube), nearly 100% of the microflora may be delivered in biologically active state directly to the target location of the GI tract, bypassing the hazards encountered through oral administration of probiotics, where only a fraction can survive. Third, unlike probiotics, most if not all of the microorganisms in FMT may be endogenous, have co-evolved, and may be fully adapted to the GI milieu to which they are delivered, and thus are typically able to survive after transplantation. Lastly, in contrast to nonspecifically mass produced probiotics, FMT can allow for selection of stool donors who are either related to and/or live with the affected individual, and thus whose GI microflora compositions have been similarly determined either genetically and/or environmentally, increasing the probability that the transplanted microflora composition will resemble that of the recipient's.

However, despite FMT's therapeutic potential in many highly prevalent and disabling conditions, including, but not limited to the epidemic of *Clostridium Difficile* infection (*C. difficile*, C. diff, or CDI), where it consistently demonstrates over a 90% cure rate in recurrent cases, a number of disadvantages in current therapeutic methods may serve to prevent its adoption in the vast majority of practice.

The general necessary sequential processes for executing FMT are as follows: First, collection of donated stool is accomplished through a requisite step of manually transferring donated stool from either the toilet bowl, freestanding commode, or other simple collection apparatus (such as a rigid plastic bowl or bag placed within the toilet) into another container. In many cases, the stool is weighed to ensure a specific and adequate amount of stool is available for processing. Excess stool is transferred into another container and disposed of. The weighed stool is transferred into a household blender or food processor. Diluents such as saline, 4% milk, or other such diluents are manually added to the mixing apparatus, and the stool is homogenized into a slurry consistency. This homogenized stool is then filtered (e.g. through a simple funnel covered with a coffee or urine stone strainer, or gauze pads) into another container, such as an enema bag, for example. Finally, the filtered liquid stool is crudely transferred from this tertiary or quaternary container into various devices such as a colonoscope (with the use of a syringe), enema kit, or nasoenteric tube for delivery to the patient. Of note, stool is a level 2 biohazard, and it is recommended that those involved in any of the aforementioned processes use universal precautions (gown, gloves, mask and eye protection), and that said processes be conducted under a laboratory hood once stool has been collected. All reusable items may then be sterilized in an autoclave or through other means, and non-reusable items disposed of. Taken together, there are many limitations to performing FMT: the process is quite unappealing (i.e. "gross") to providers, patients and donors, carries significant risks of insanitation (for the user and environment) and contamination (of the stool sample and microflora), has highly unappealing aesthetics, and is burdensomely inefficient with regards to carrying out the sequential processes. There is also no simple or standardized protocol, ensuring reliably repeatable formulations are produced. Further, it can be desirable to advance methods of fecal biotherapy so that it can delivered through more diverse and appealing processes, where the microflora must be significantly refined and isolated for potential incorporation into modes of delivery such as capsules, foods, or liquids for oral consumption. Under the current methodology, such modes of delivery are neither practical nor appealing.

Because there have been no technological innovations developed to specifically or comprehensively address the sequential processes required for FMT, the following resultant overarching limitations have dramatically discouraged the adoption of this highly effective therapy in the vast majority of practice:

Risk of Insanitation (for the user and environment) and Contamination (of the stool sample and microflora): Because the prior art requires that stool is collected, transferred, processed, and cleaned in a largely "open-system", where the user and environment are repeatedly exposed to the stool and vice versa, there is significant risk of insanitation (for the user and environment) and contamination (of the stool sample), respectively.

Unappealing Aesthetics (of performing necessary sequential processes): While the general concept of this therapy alone is inherently unappealing to all parties involved, it is also somatically abrasive throughout the entire sequence of processes, as the stool is visible, and the stool's malodor is unmitigated. Further, and with respect to further limitations described below, without effective methods to refine and aesthetically improve microflora from stool, it will not be possible to advance delivery methods for FMT where the target component (microflora) can be delivered through other mechanism where visible appearance, taste, smell, and/or potency (or concentration) are salient features.

Inefficiency (of performing necessary sequential processes): As a result of the numerous necessary separate sequential collection and preparation steps, the various required apparatuses, the subsequent need to clean said apparatuses, and the required protective gear and dedicated space to carry out said preparation and cleaning, the overall process of executing FMT may be quite inefficient. Such inefficiency may not only problematic as it can relate to the previous two major aforementioned limitations above, but also because in practice it may often be impractical and time consuming for the various users involved.

Indeed, in considering the relevance of described prior art to the aforementioned limitations of FMT, it can seem that such current methodologies can offer only partial mitigation of some aspects relating to the risk of insanitation and contamination, and unappealing aesthetics (such as can be provided through various stool collection devices), while failing to significantly address the limitation of inefficiency all together. Further, to the extent that current methodologies can mitigate the limitations of risk of insanitation and contamination, and unappealing aesthetics, said mitigation may address only the collection process, and may not address these limitations within the requisite subsequent steps involved in FMT—processing the stool, isolating the microflora, and delivering the microflora to the patient.

While various innovations in stool collection devices have been designed to mitigate certain undesirable limitations of stool collection, generally for the purpose of improving the process of collecting and preserving donated stool samples for subsequent analysis (such as diagnostic tests), none are adapted for the unique needs of FMT, or advancements thereof. Certain innovations in stool collection devices have attempted to further decrease unwanted contamination of stool by urine, improve transportation function, and allay some unappealing aesthetic aspects of stool odor and visualization after stool donation (U.S. Pat. No. 6,351,857 and U.S. Publication 2008/0108961). There have also been a wide variety of devices and methods developed for the purpose of processing stool samples, again typically for the purposes of subjecting the stool sample to a diagnostic test. The stool collection device is generally separate from the stool processing device, and thus necessitates transfer of the stool from the former to the latter. There has been an attempt to incorporate a processing mechanism directly within a disposable in-toilet stool collection device designed with built-in motor-driven blades, and the ability to infuse fluid through ports for stool homogenization, as well as a valve outlet for dispensation (U.S. Pat. No. 4,101,279). However, while intended to offer certain conveniences in stool collection and processing, this stool collection device was, similar to the vast majority of other stool collection devices, intended to aid subsequent diagnostic applications, and had no proposed applications for FMT. As such, it can have many shortcomings with respect to effectively performing and advancing FMT, if one were to propose such an adapted application. The stool collection device generally lacks any method for refining the stool, microflora, or filtrates thereof in any way. Additionally, while it may the capacity to crudely transfer contents from within the container through a conduit, it is not designed specifically to offer any method of delivering FMT efficiently to a recipient's colon either directly or indirectly within a closed system. It also would seem that in the principal described embodiment with a conventional metal blender blade, this device not only can have the significant potential to place the stool donor at risk of injury, but may be limited in scope with respect to modes of performing homogenization and stool processing. This device may also not be designed to accommodate varied amounts of stool and diluents, where fixed ratios may require large volumes of substance be sealed within the container. Where condensing the size of the device may be reliable for storage or shipping of contents, the device seems to lack any mechanism for reducing its size, or adapting its conformation.

It is thus desirable to provide a device that overcomes the aforementioned limitations by allowing for the necessary sequential processes of FMT (i.e. direct stool collection, liquification and homogenization, comprehensive microflora isolation and refinement, and microflora delivery to recipient) to be performed in an efficient and sanitary manner within a closed system, and that offers mechanism of advancing delivery methods of FMT.

SUMMARY OF THE INVENTION

Embodiments of the present invention overcome the disadvantages of current methods and systems by providing a closed system for the collection, processing, storage and transportation of donated stools for use in biotherapy involving collected gastrointestinal microflora for the treatment of a variety of morbidities in humans and animals.

In an illustrative embodiment, a collection device comprises a toilet bracket having a central ring to hold a collection container. The toilet bracket has a plurality of arms to position and holds the collection device. The collection container may be placed within the central ring and may be constructed and dimensioned so that the container will not fall through the central ring.

The collection container can be removed from the ring after the donated stool has been deposited within the container. A cap with a valve and nozzle can be placed onto the container and sealed to create a "closed system". Various agents can be added by various methods to the contained stool to achieve dissolving, colorizing, deodorizing or to add further therapies. An agitator is located in the bottom of the container according to an embodiment. The agitator can be placed in other locations on the container.

The container may be constructed of a hard, non-porous plastic. In alternate embodiments, the container can be formed of elastomeric polymers, rubber or other materials that create a bag, a syringe or other structures. In a further alternate embodiment, the container can be provided with an agitator, a main chamber and a cap with filters, nozzle and valve. The agitator has a drive shaft that engages a male gear located on a base station.

The cap can be provided with one or more filters to create a multi-stage filter system.

The base station comprises a drive motor to interact with the agitator on the container. When the container is engaged to the base station and the motor is engaged, the collected stool can be agitated, homogenized and filtered to create the desired solution containing microflora in the desired consistency. This solution can then be dispensed directly into the patient's GI tract via enema or nasoenteric tube, or can be transferred within a closed system to other delivery apparatus such as a colonoscope for administration into the receiving patient.

In alternate embodiments, the container can be a sealable bag, or a standalone toilet. A large syringe or disposable catheter can also be utilized to collect and process microflora, and to administer the processed microflora solution into the receiving patient's intestinal tract.

An aspect of the invention provides a method of isolating gastrointestinal microflora from stools of a donor. Stool can be collected from the donor in a container as the donor is defecating, typically while on a toilet seat. The container may be sealed to place the collected stool in a closed, typically anaerobic, environment. A solvent can then be introduced through an introduction port into the sealed container. The solvent and collected stool can then be homogenized within the sealed container to form a mixture. The homogenized mixture can be filtered to extract a filtrate comprising the solvent and gastrointestinal microflora from the mixture within the sealed container. The filtrate has reduced solids, for example, a reduced ratio of weight non-living solids to weight of living solids of no greater than about 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10%. Typically, the filtrate is dispensed from a dispenser port in the stool container, which may be the same as the introduction port.

Stool will typically be collected from the donor as the donor is defecating while seated on a toilet. The container may be isolated from an environment of the toilet, for example, by being closed to toilet water while stool is collected such as by using various flexible sheaths. A linking mechanism or bracket may be provided to couple the toilet seat for the donor to the container for collecting stool.

The container will typically be configured to accommodate a variable volume of stool and solvent. For example, the container may be at least partially made of an expandable material or be collapsible. The container may be at least partially opaque to provide an improved aesthetic than if the container were transparent. The container may also include a vent for gases to escape and that vent may have a deodorizing filter such as an activated carbon filter. The container may be sealed by closing an opening in the container from which stool is collected and applying a negative pressure through a suction port in the container to remove air from the container. In some cases, the suction port is the same as at least one of the introduction port or dispensing port. Certain gases or other substances may be added to encourage an anaerobic or otherwise ideal environment to sustain viability or promote growth of the microflora contained within.

The solvent added to the stool may comprise one of saline, milk, or other sterile (or non-bacteriostatic or bacteriocidal solution) solvent. The volume of solvent introduced may result in the homogenized mixture being of a predetermined density. The container with the collected stool may be weighed to determine the weight of the collected stool and the volume of solvent introduced would depend on the determined weight. Having any homogenized mixture being of the same density may be useful for quality control purposes, for example, if it is desired to demonstrate reproducibility for regulatory, safety, or efficacy purposes, or to collect microflora from multiple donors to create or establish a microflora bank or repository.

The solvent and collected stool may be homogenized by applying external physical force to the container. The container may comprise a flexible bag and the solvent and collected stool may be homogenized by placing the flexible bag in at least one of a roller mechanism, a mashing mechanism, paddle blender, or other such method. Other methods of homogenization may include shaking the container with a device similar to a paint mixer. In some specific devices, the solvent and collected stool may be homogenized by actuating a mixer within the container.

To filter the homogenized mixture, it may be passed through at least one, typically two filters. The pore size of the second filter may be smaller than that of the first filter to help minimize any clogging of the filter pores. For example, the first filter may have a pore size of at most 4,000 μm or 2,000 μm and the second filter may have a pore size of at least 0.22 μm or 0.44 μm which would only let solids at least as small as bacteria or other microflora microbes to pass. Filtration may be facilitated by physically pressing the homogenized mixture against the filters. This may be useful in cases where there is only a single filter with a pore size in the range of 0.22 μm to 4,000 μm.

Aspects of the invention also provide systems and devices adapted and configured for performing the above method. For example, a system for isolating gastrointestinal microflora from stools of a donor may comprise a container for collecting stool from the patient as the patient is defecating and holding the collected stool in a closed, typically anaerobic, environment, means for homogenizing a solvent and the collected stool into a mixture within the closed environment of the container, and means for filtering the homogenized mixture to extract a filtrate comprising the solvent and gastrointestinal microflora from the mixture. Again, the filtrate has reduced solids, for example, a reduced ratio of weight non-living solids to weight of living solids of no greater than about 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10%. The system may further comprise a linking mechanism for coupling the stool collection container to a toilet seat and means for determining the weight of the collected stool in the container.

The container of the system will typically be configured to accommodate a variable volume of stool and solvent, for example, by being at least partially made of an expandable material or be collapsible. The container may comprise an at least partially opaque exterior. The container will have an opening for receiving the stool that can be sealed airtight. The container may have various ports such as an introduction port for the introduction of solvent, a dispensing port for the dispensing of the filtrate, and a suction port. Two or more of these ports may be the same. The container may also comprise a vent mechanism having a deodorizing feature such as an activated charcoal filter.

The container may comprise any number of structures. For example, the container may comprise a flexible bag for which the means for homogenizing the solvent and the collected stool comprises at least one of a roller mechanism, a mashing mechanism, a paddle blender, or other such method adapted to apply an external physical force to the flexible bag.

The means for filtering the homogenized mixture may comprise one or more filters within the means for collecting and holding stool, which may have a pore size of at least 0.22 μm to at most 4,000 μm. Often, the means for filtering the homogenized mixture further comprises a filter clearing mechanism. The means for filtering the homogenized mixture may comprises a plunger for pressing the homogenized mixture against the one or more filters.

Aspects of the invention also provide various devices for collecting and isolating gastrointestinal microflora from stools of a donor. One such device may be a container comprising a first compartment for collecting and holding stool, a second compartment for holding a filtrate, a filter separating the first and second compartments, and a mixer in the first compartment for homogenizing an introduced solvent and the collected stool into a mixture. The container may further comprise a cap or other mechanism for sealing an opening in the first compartment through which stool is collected. The filter may comprise a first filter and a second filter having a smaller pore size than the first filter. For example, the first filter may have a pore size of at most 4,000 µm or 2,000 µm and the second filter may have a pore size of at least 0.22 µm or 0.44 µm as described above. The mixer of the container may be adapted to be coupled to an external actuator for actuating the mixer. A clearing mechanism may be provided and disposed adjacent the filter to be coupled to the external actuator for actuating the clearing mechanism to clear the filter. The container may further comprise a plunger in the second compartment for advancing and pressing the filtrate through the first compartment. The plunger may comprise a port for filtrate to pass through the filter and into the second compartment. The second compartment may comprise a dispensing port for dispensing the filtrate.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

The invention description below refers to the accompanying drawings, of which:

FIGS. 16A to 16C show a filtrate refinement system according to an alternate embodiment;

DETAILED DESCRIPTION OF THE INVENTION

Figure 1:
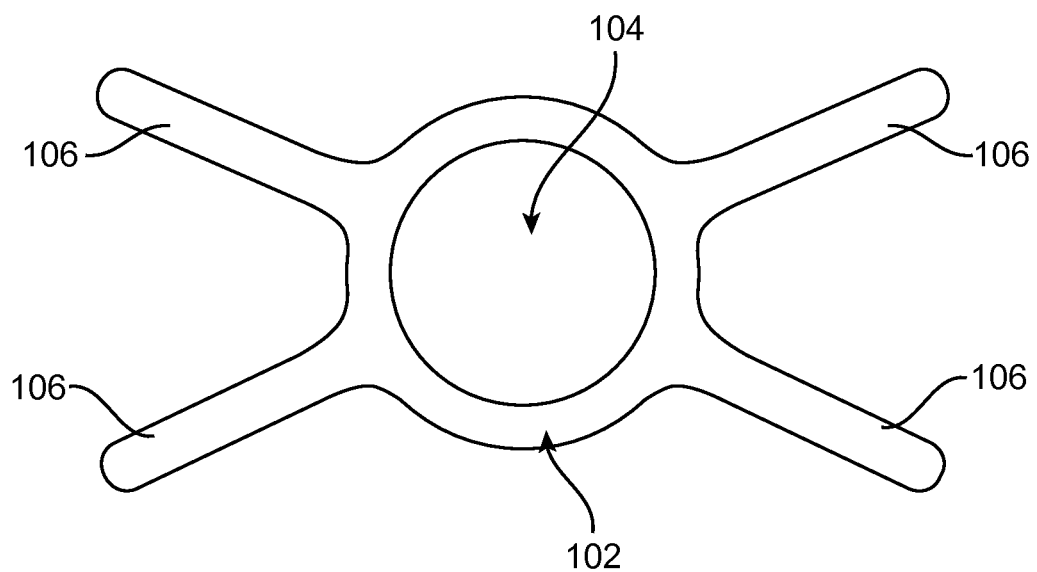
FIG. 1 is a top view of the toilet bracket for the collection of stool samples according to an illustrative embodiment.

FIG. 1 is a top view of the toilet bracket for a stool collection container according to an illustrative embodiment. A toilet bracket 102 can be dimensioned appropriately to fit standard sized toilet bowls. The central ring 104 on the bracket that holds the collection container (not shown) in place. A plurality of arms 106 are provided on the bracket that extend outward from the central ring 104 towards the edge of the toilet bowl. In the illustrative embodiment, the bracket 102 has four arms 106. In alternate embodiments, there can be more or less arms provided. A disposable collection container can be seated inside the central ring 104, in the proper position for the easy collection of a stool sample. The bracket 102 can include a repositioning apparatus that allows the donor to move the device towards or away from the rear of the toilet while seated. This can allow the user to adjust the mechanism to their unique anatomy and avoid urine contamination with the apparatus while allowing any paper waste used by the donor to be directly deposited into the toilet bowl. The ring 104 may hold the device out of the water at the bottom of the toilet bowl and away from the donor's exposed skin and paper waste. The diameter of the ring can correspond to a lip near the top of the disposable device 302, described more fully in FIG. 3 below.

The disposable device 302 can be positioned so that the top of the container lies flush with the top face of the bracket 102. Locking the disposable device 302 into the bracket ring 104 can also be accomplished by designing the disposable device with a top diameter that can exceed that of the ring, preventing it from passing all the way through the central ring. Alternatively, this can be accomplished through the use of a counterbore, or partial counterbore in the bracket which interferes with threads on the disposable device, or with a ridge in the disposable device below the threads. The disposable device 302 can also be screwed into the central ring 104, or releasably attached to the ring through other alternative methods. In an alternate embodiment, it is expressly contemplated that the entire bracket 102 can be permanently connected to the container 302 and provided as one solitary unit.

Figure 2:
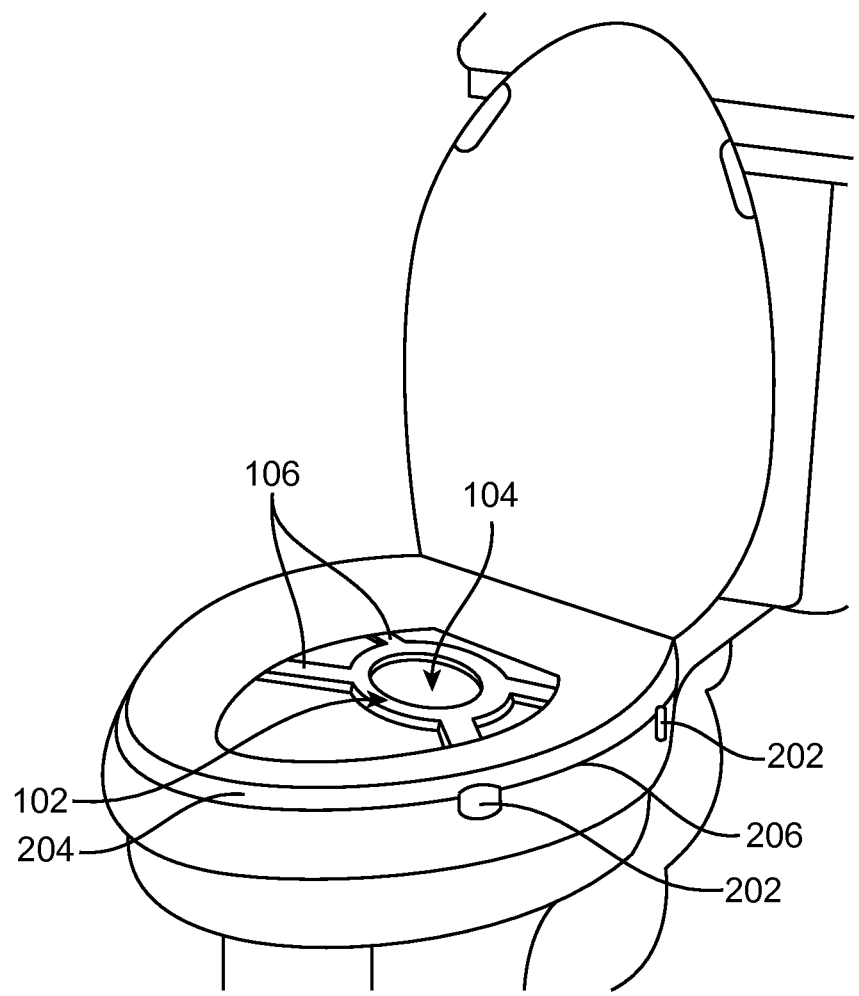
FIG. 2 is an isometric view of the bracket of FIG. 1 installed into a standard toilet seat according to an illustrative embodiment.

FIG. 2 is an isometric view of the bracket after installation into a toilet seat according to an illustrative embodiment. Tabs 202 are positioned at the end of each of the arms 106 that hold the bracket 102 in place between the upper surface of the toilet bowl 206 and the bottom of the lowered toilet seat 204. The bracket arms 106 can be orientationally angled and dimensioned to accommodate the various dimensions of a toilet bowl seat. The tabs 202 can be designed to extend vertically past both the bowl 204 and the toilet seat 206 so that it cannot slide or rattle in place.

Figure 2A:
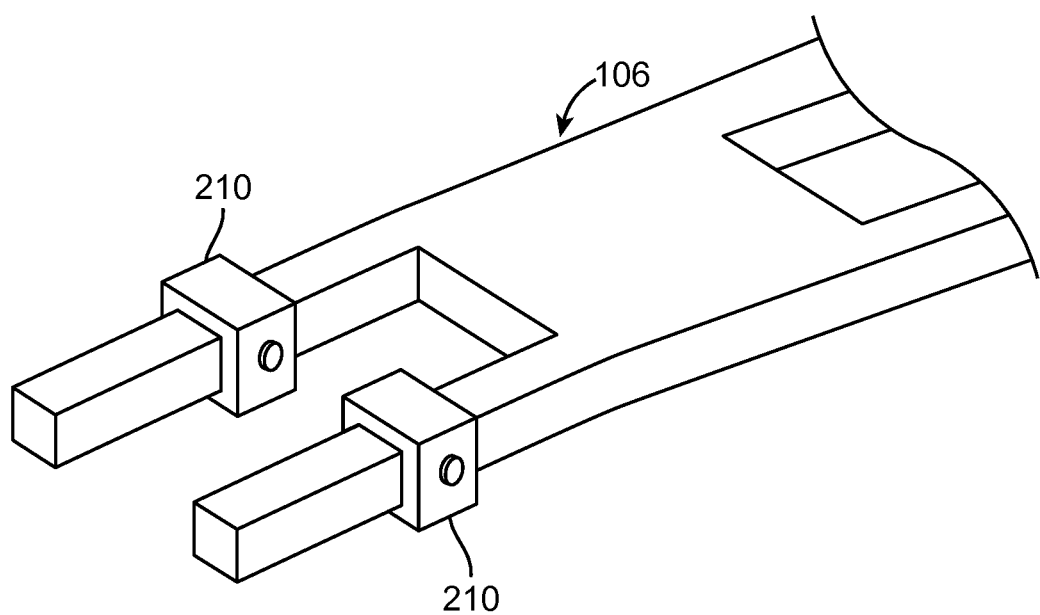
FIG. 2A is a view of the bracket of FIG. 1 with a locking system according to an alternate embodiment.

FIG. 2A is an alternate embodiment in which the arms can extend horizontally beyond the toilet bowl, and contain moveable and/or lockable tabs 210 that slide on the arms to lock the bracket in place once positioned. The bracket 106 can be composed of non-allergenic plastic, and be designed to resist slipping once positioned on the toilet. This can be achieved with pads composed of rubber or another material that can provide friction between the bottom of the bracket 106 and the bowl of the toilet 204.

Figure 2B:
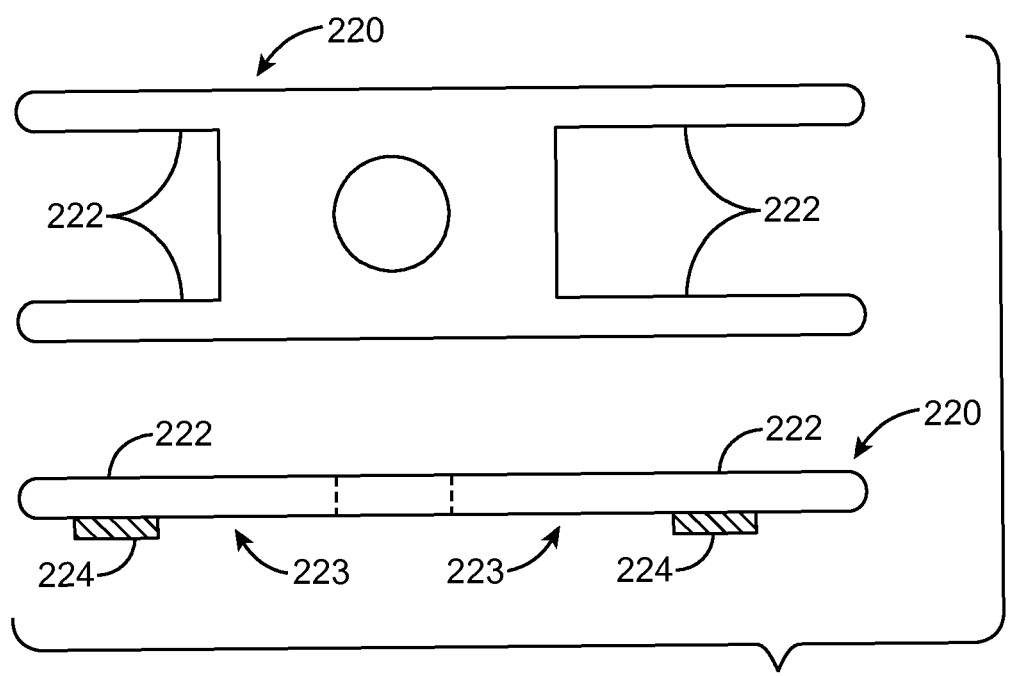
FIG. 2B is a set of views of a toilet bracket having a segment of tacky polymer and/or a tape-like adhesive attached to the bottom surface of each arm according to an alternate embodiment.

FIG. 2B is an alternate embodiment in which an exemplary bracket 220 has a plurality of arms 222 that have their bottoms 223 surfaced with a tacky polymer or tape-like adhesive 224. The bracket 102 can be light in weight so that it can be easily detached and transported from one toilet to another. The bracket 102 can be reused between collections with standard cleaning and sanitization procedures, but can also be disposed of. In further alternative embodiments, FIG. 2C discloses an exemplary rigid bracket 230 that can sit atop the toilet seat 236, and can be secured to the toilet seat 236 with heavy duty adhesive strips 234 that are attached to each of the arms 232.

Figure 2C:
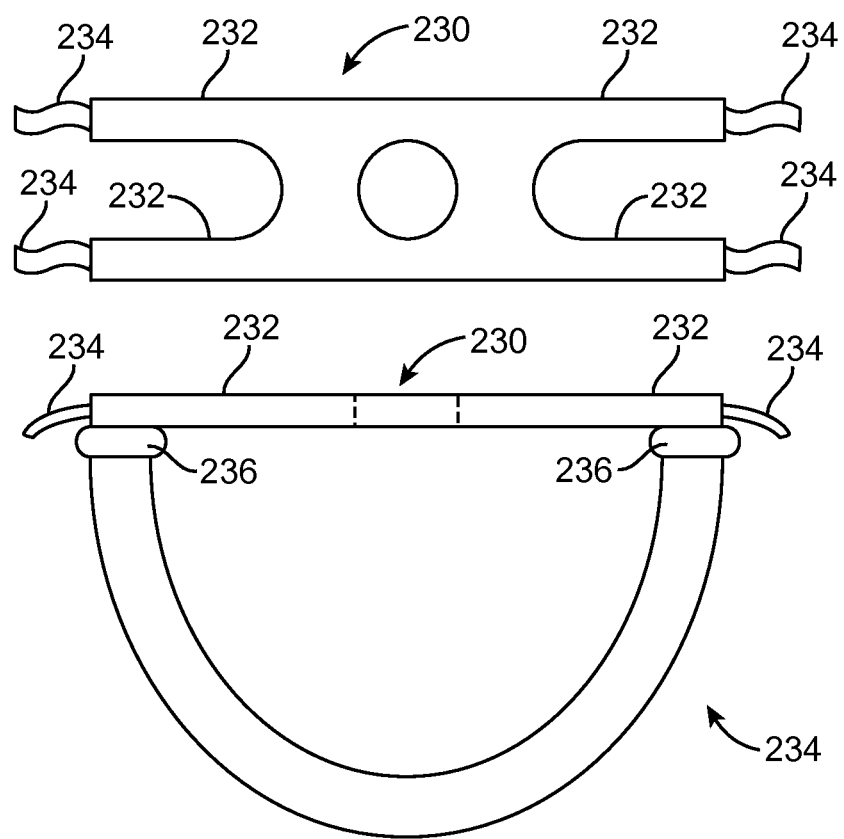
FIG. 2C is a view of a rigid toilet bracket with adhesive strips attached to each of the arms according to an alternate embodiment.
Figure 2D:
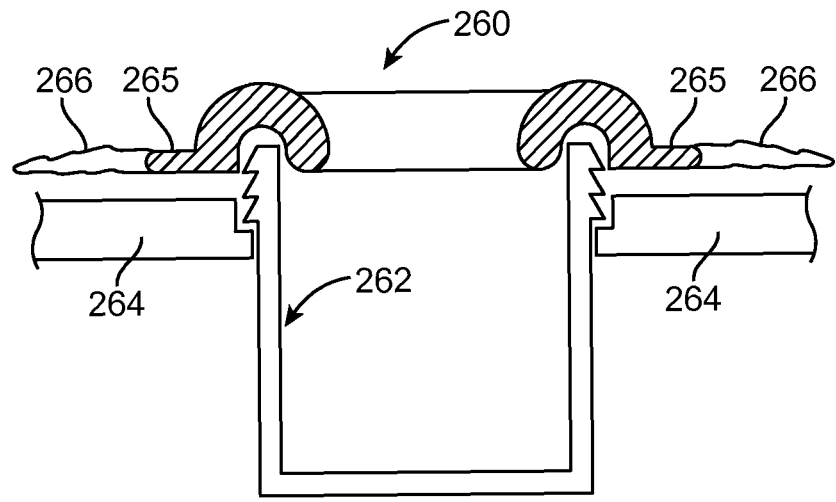
FIG. 2D is a side view of a toilet bracket with a retained container having a disposable cover according to an alternate embodiment.

FIG. 2D discloses a separate disposable component 260 that can be used to cover the top of the disposable device 262, as it sits in the bracket 264, serving to prevent contamination of the outside of the disposable device 262 according to an alternate embodiment. The cover 260 can be designed to be compatible with the top portion of the disposable device either being flush with the top of the bracket 264, or raised above the bracket by approximately 0.25" (or another functionally superior height). The cover 260 can be constructed of a rigid plastic, or a baglike sleeve 266, and can incorporate a rigid feature which lightly engages with the top portion of the disposable device.

Figure 2E:
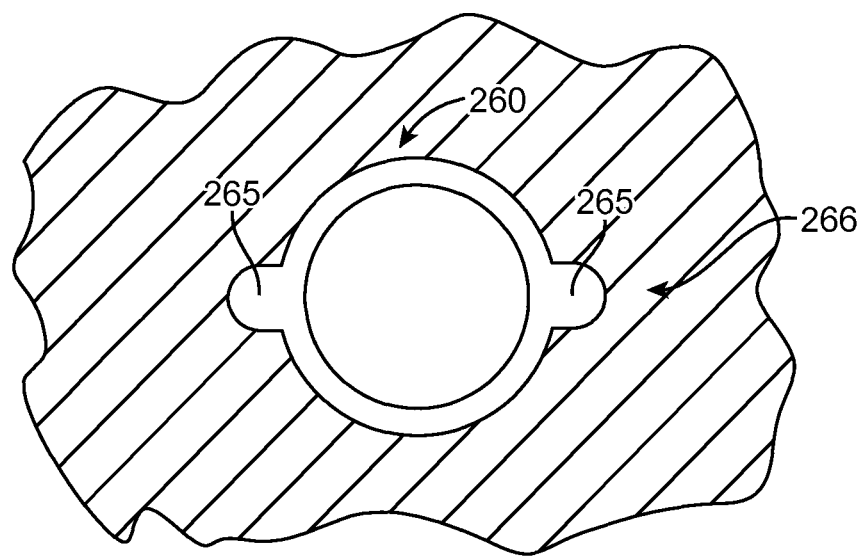
FIG. 2E is a top view of the cover of FIG. 2D that has been furnished with handles according to an alternate embodiment.

FIG. 2E describes an alternate embodiment in which the cover 260 of FIG. 2D that has been constructed with handling tabs 265 for ease of removing the cover 260 from the disposable device 262. The cover component can then be discarded after stool collection is complete. In additional alternate embodiments, the on-toilet device can include a removable, rigid or bag-like cover that protects the exterior of the container from contamination where it is exposed to the interior toilet bowl environment.

Figure 2F:
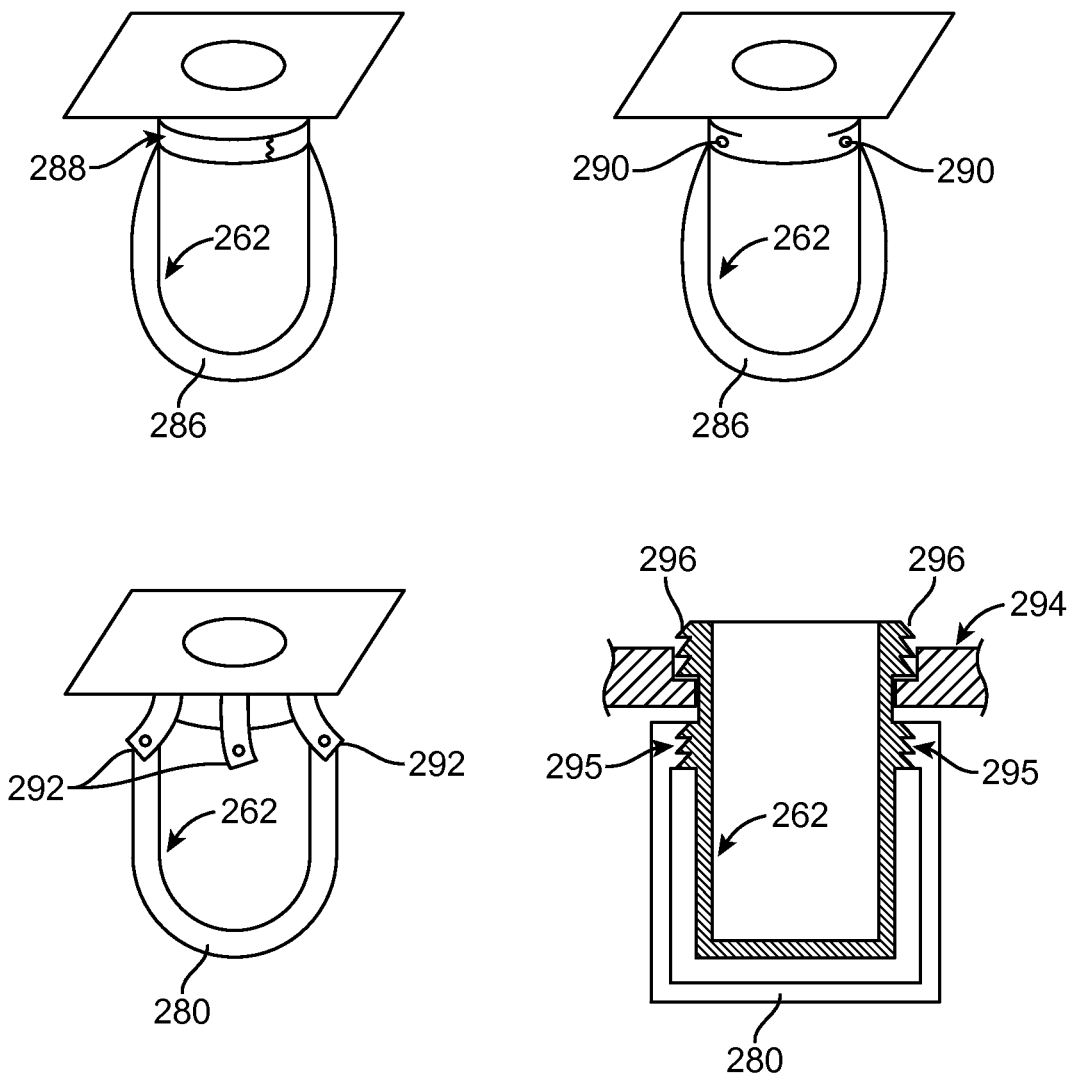
FIG. 2F is a set of views that depict various implementations of a bag-like cover for the container according to an alternate embodiment.

With reference to FIG. 2F, a bag-like cover 286 can be temporarily attached to the container by various methods according to an alternate embodiment. For example, a heavy duty adhesive tape 288 is permanently or releasably attached to the cover 262. In alternate embodiments, the attachment of the cover 286 to the container 262 can be accomplished using perforated tabs 290 or molded snaps 292. A rigid cover 294 can also be attached to a rigid container 262 or rigid component of a non-rigid container via an extra set of threads 295 on the rigid portion of the container below the upper threads 296.

Figure 3:
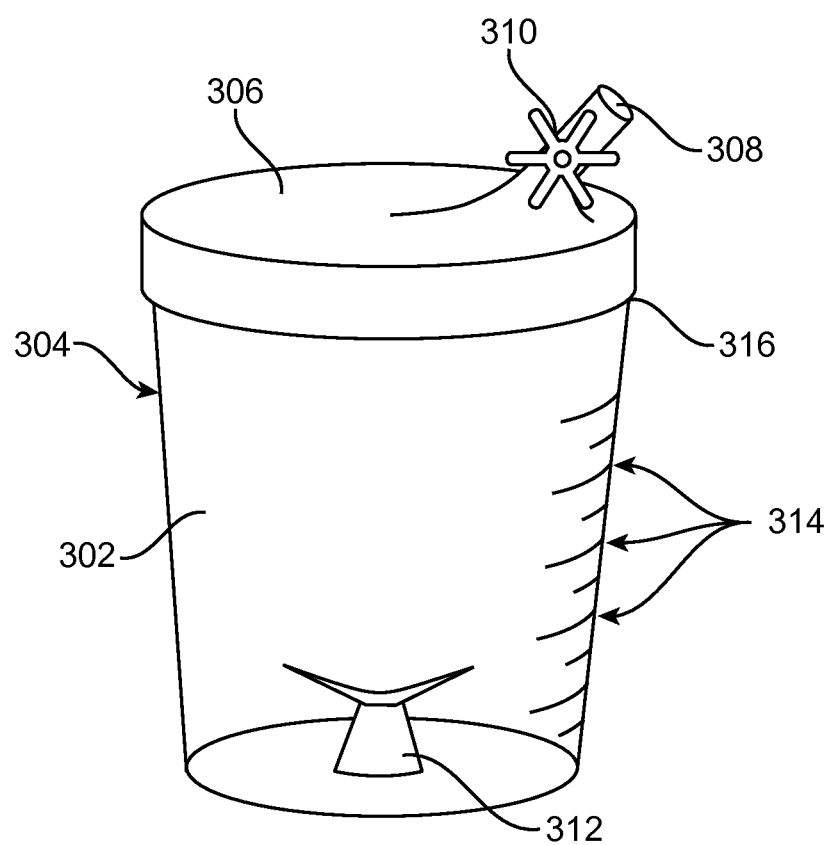
FIG. 3 is an isometric view of the disposable device according to an illustrative embodiment.

FIG. 3 is an isometric view of the disposable device 302 according to an illustrative embodiment. The illustrative device 302 can be composed of several components. The body 304 of the device is a "container", and can be inserted into the ring 104 on the toilet bracket 102. The container cap 306 contains a nozzle 308 controlled by a manually adjustable valve 310. Said nozzle and valve can be a luer-lock and/or luer valve, an attachable/detachable luer taper or luer slip, 3-way stopcock, or a different device that serves the same function. In alternative embodiments, the nozzle/valve can be collapsible and manually raised and lowered to allow flow, can be composed of flexible tubing instead of a hard plastic to allow it to be bent and stored within the cap 306.

FIG. 3 shows a "closed system" for containing donated stool. Once the cap 306 is placed on the container 304, or another alternative method of sealing the container are performed, an air and watertight "closed system" for processing and subsequently dispensing the collected stool components has been established. Prior to or subsequent to processing, and prior to therapeutic use of the donated stool, the stool can be subjected to a pre-treatment screening for the presence of undesirable content. Methods for performing the pre-treatment screening for stool pathogens can include, but are not limited to, the detection of *C. difficle* toxins A and B, *Giardia, Cryptosporidium* and *Helicobacter pylori* antigens, ova and parasites, routine bacterial enteric pathogen bacterial culture, and other infectious or potential harmful unwanted contents, and can be included as a feature within the closed system of the device, or provided as a separate kit tailored to couple with the device. This screening can utilize methods currently available or those subsequently developed. In addition, prior to or subsequent to processing, and prior to therapeutic use of the donated stool, the stool can be subjected to a pre-treatment analysis to validate or otherwise assess the microbiome composition and/or activity, small molecule content, and/or other elements contained within the stool. Such analysis can be performed through such methods as standard culture techniques, assays or blots, PCR or non-PCR techniques, DNA microarrays, other genomic or next generation sequencing techniques, integrated microfluidics technologies, and/or similar technologies currently available or subsequently developed in the art to assess the content of the stool at the molecular level. These analytic techniques can also include the use of specific software and other integrative technologies serving to evaluate and describe the microbiome and/or other desirable contents of the donated samples. Such analytic features can be included as a feature within the closed system of the device, or provided as a separate kit tailored to couple with the device.

The precise weight of the donated stool can be determined by integrating a scale, or a variety of potential weighing methods within the device or components coupled with the device. The ability to measure the precise weight of the donated stool allows for determination sample adequacy as well as calculated addition of various agents to achieve specific standardized or otherwise desired ratios and compositions of the stool with said agents. Said ratios may also be determined through other measurement techniques that do not rely on the weight of the stool sample and can be included at any point subsequent to stool donation. If such standardized ratios are desired, the device, or components coupled with the device can provide the user with algorithm-based instructions on how much of each various agent can be added based on the measured weight of the donated stool sample. Said algorithm and instructions can be provided through methods including, but not limited to a complementary written pamphlet, illustrations on a surface of the device itself, automated weight-based calculations by software or other methods within the device or a component coupled to the device with instructions displayed digitally, or by other visual mechanism.

Agents such as saline and/or other dissolving, buffering, colorizing, deodorizing, mucolytic agents, or other liquid, solid, or gaseous agents desired for different properties including, but not limited to those for aesthetic improvement, encouragement of an anaerobic or otherwise ideal environment to sustain viability or promote growth of the microflora, diagnostic screening, or sample analysis can also be introduced to this closed system through various methods. Said methods of introducing these agents can include, but is not limited to syringe introduction through a valve 310 located in the cap 306 or valves included elsewhere on the cap 306 or container 304, or through sealed compartments incorporated within the walls of the container 304, cap 306 or other attachments incorporated or coupled as confluent features of the closed system.

Access ports specifically designed to interface with currently or subsequently available saline containers and/or other premixed solutions of various agents of standardized quantities (i.e. 50 ml, 100 ml, 250 ml, 500 ml etc.) can also be included as a feature of the device. Such a feature can include, but is not limited to a similar mechanism to those of a free-standing water dispenser, whereby the container of fluid is placed into the device upside-down, forcing a probe contained within the port of the device to puncture the cap of the fluid container, allowing the flow of fluid from the container into the device. In alternative embodiments, the device can have an access port with tubing connected to a capping feature, which can be placed on the uncapped fluid container and allow the fluid to flow from the container to the device upon turning the container upside-down. Regardless of the embodiment, upon disconnecting the container of fluid from the device, the port on the device reforms an air and water tight seal. Agents contained in said compartments can be introduced within the interior of the closed system apparatus through the use of an applied force from the exterior of the closed system, by manipulations serving to puncture sealed barrier material, or through other similar mechanisms. A closeable vent may also be provided to aerate the contents of the fluid container. Such a vent may include an activated carbon or other deodorizing filter so odors and gas from the vent does not offend the handler of the container.

An agitator 312 can be incorporated into the bottom of the container 304, or elsewhere, such as along the sides or top of the container. The agitator 312 is used to homogenize the stool sample with the aforementioned added agents. Potential methods of agitation include, but are not limited to, conventional blending (as depicted herein), mechanically aided straining (similar to a garbage disposal), manual or device-assisted internal or external mechanical compression, shaking, or screen filtering. The container 304 may be provided with a set of measuring lines 314 that can be used to ensure that the proper amount of various agents have been added after the stool has been collected and after homogenization. Said lines also ensure that an adequate amount of homogenized stool solution has been produced subsequent to processing. The lip 316 of the container 304 that interacts with the ring 104 on the removable bracket 102 to secure the container in place. Stool can be collected by the container 304 as the donor is defecating. While collection occurs, the collection container 304 may be protected from the outside environment of the toilet, for example, such that urine and toilet water will not find their way into the collection container 304. For example, the collection container 304 may be spaced away from the toilet water and the opening of the collection container 304 may be aligned so as to collect only stool from the donor. After stool is deposited into the collection container 304 by the donor as the donor is sitting on a toilet seat and defecating, the cap 306 seals the sample from exposure to the surrounding environment. Said sealing can be accomplished through a variety of methods.

The container 304 can be composed of a hard, non-porous plastic and, when sealed, creates a closed system that is completely air and watertight. In alternative embodiments, the container 304 can be composed of an elastomeric plastic or rubber material to more closely resemble a bag (as will be more fully described below), can take a form resembling a syringe, or can be composed of various other materials or structures. The container 304 may have an opaque exterior to provide a pleasing, more aesthetic look and feel when used to collect and store stool. The container 304 can be partially transparent so that a silhouette of the contents can be seen from the outside for comparison with the measurement lines 314, but can also be moderately opaque so that the contents inside are not visible in detail. The interior of the container 304 can also be treated with odor blocking agents such as carbon, or other useful agents. The container itself may be made of a material which is itself deodorizing or "odor proof". The shape of the container 304 can include a parabolic loft design or other contours to optimize homogenization and subsequent filtration. Such a design can take the more conventional shape of a household blender, and can include vertical ridges on the interior walls of the container to facilitate a vortex of the sample towards the homogenizing component.

Figure 4:
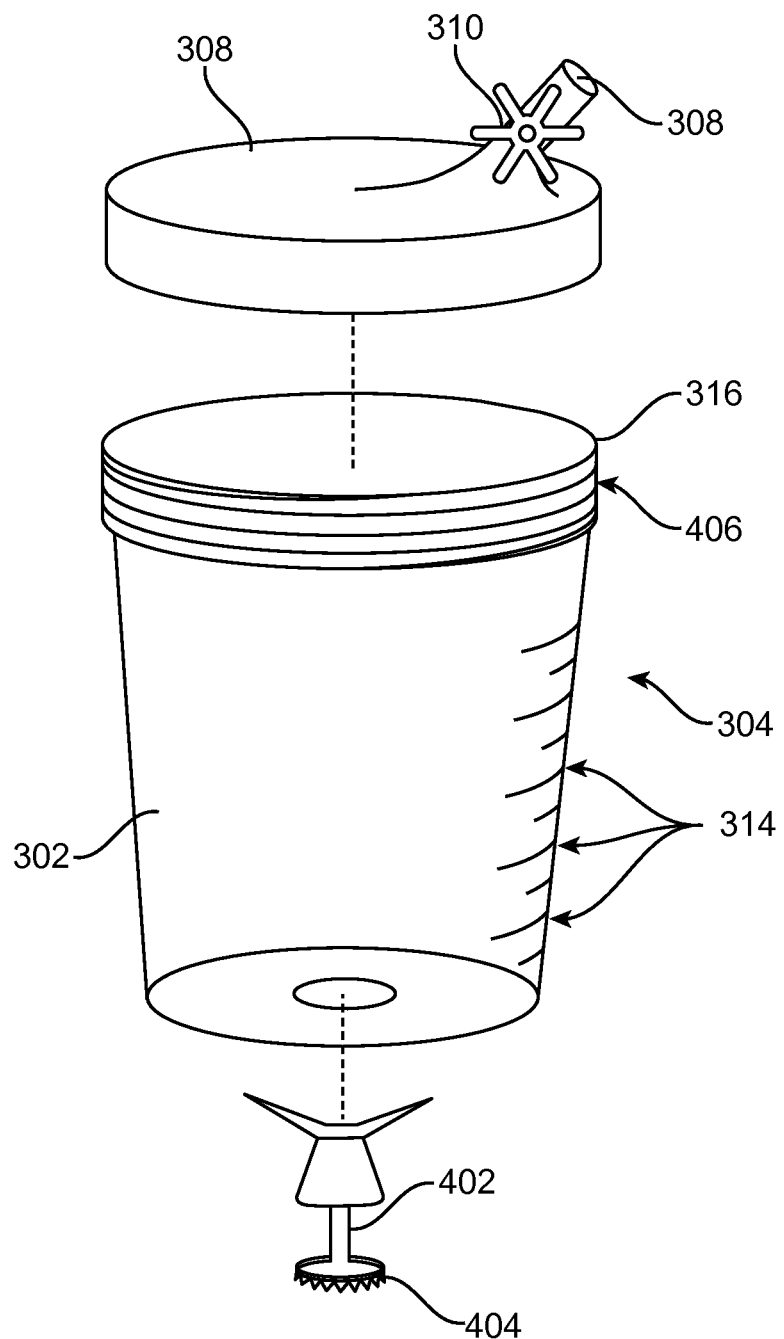
FIG. 4 is an exploded diagram of the disposable device of FIG. 3, detailing the agitator, main chamber, and cap with filters, nozzle, and valve according to an illustrative embodiment.

FIG. 4 is an exploded diagram of a potential embodiment of the disposable device, detailing an agitator, main chamber, and cap with filters, nozzle, and valve according to an illustrative embodiment. An exemplary drive shaft 402 can connect a motor to the agitator 312 within the container 304. A female gear 404 that engages with the male gear (not shown) on the base station (described more fully below) to turn the agitator. In alternate embodiments, this gear coupling can be accomplished using a magnetic coupling in which the agitator is contained within the container and a complete seal is achieved. The gears can interact such that there may be a tight connection between the base station 602 and the agitator 312, and will prevent any slipping between the gears, as well as keep any solution from escaping the bottom of the container 304. The agitator can be non-removable and composed of the material as the rest of the device, and can be manufactured into each unit so that it can be disposed of collectively. Alternatively, the agitator could be removable from the container, or could be introduced into the container through various mechanisms, including, but not limited to being pierced through a self-healing membrane on the base of the container, or locked into the container prior to stool donation. A set of male threads 406 on the top portion of the container 304 that can be used to secure the cap 306 in place, though many other methods of securing the cap to the container can be used in alternative embodiments. In one such alternative embodiment, the cap 306 can include a circumferential lip (not shown) on the bottom of the cap that rests snugly over the container 304. In such a design there can be a channel (not shown) that houses a rubber O-ring (not shown), into which the container 304 presses to form a circumferential seal. Such a design can include two protruding slots (not shown) on the left and right of the cap 306 allowing latches on the container 304 to lock the two parts together and engage the entire circumference of the seal. It is further contemplated that an additional feature can include a cutout (not shown) on the front of the cap 306 which interfaces with an alignment tab (not shown) on the container 304, providing for a proper seating of the components.

Figure 5:
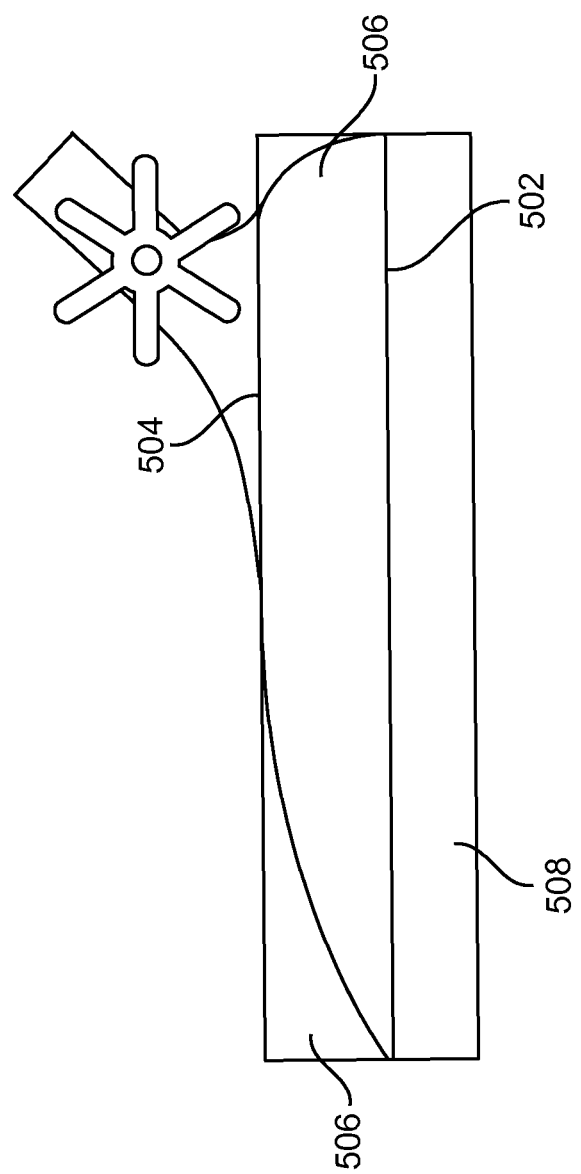
FIG. 5 is a cross section view of the cap of the disposable device of FIG. 3, detailing its interior shape and design according to an illustrative embodiment.

FIG. 5 is a cross section view of the cap, detailing its interior shape and design according to an illustrative embodiment. Primary 502 and secondary filters 504, comprise a "multi-stage" filter system used to filter non-homogenized stool components from the rest of the solution and to selectively permit the passage of microflora, respectively. The addition of the primary filter(s) 502 with larger pore sizes can help prevent clogging of the secondary filter(s) 504 and can provide a higher quality of homogenized solution for subsequent delivery methods. Specifically, secondary filters 504 with pore sizes that allow only or primarily microflora components to pass through it can be incorporated to further isolate and collect microflora. Additional secondary filter types which selectively retain certain or all microflora contents to pass through including, but not limited to those made from borosilicate microfiber (or other similar materials), other membrane filters, or other filters known to the art, can be included within or separate from the multi-stage filter system. Towards that end, said multi-stage filters can be comprised of a plurality of one or more sequential primary and secondary filters, with various pore sizes and made of a variety of materials, separated by various distances, and oriented in various positions with respect to one another, or with respect to themselves (i.e. in a pleated configuration). Said multi-stage filters can be located anywhere within the closed system (any potentially confluent space contained within an air and watertight seal from the environment formed by the device and/or components added/coupled in confluence), depending on the embodiment.

Regardless of the location, the filtering apparatus can include methods for allowing or disallowing fluid or air to pass through the filter(s). Such a method can include, but is not limited to a slide or twist lock on the exterior of the apparatus that moves a nonporous material over the top or bottom of the filter(s) within the closed system. An activated charcoal or other deodorizing filter may be provided adjacent to this moveable nonporous material so that gases escaping from the filter(s) does not offend the handler of the container 304. Similar variations of such methods can also be incorporated to aid the efficiency of filtration through continual or intermittent agitation of the filter(s) or substances in contact with the filter(s). By moving a component such as a brush, screen, or other component on the filter(s) surface, or moving the filter(s) surface against said components, such methods can facilitate filtration efficiency by removing or disturbing contents which can be clogging the filter pores.

Figure 5A:
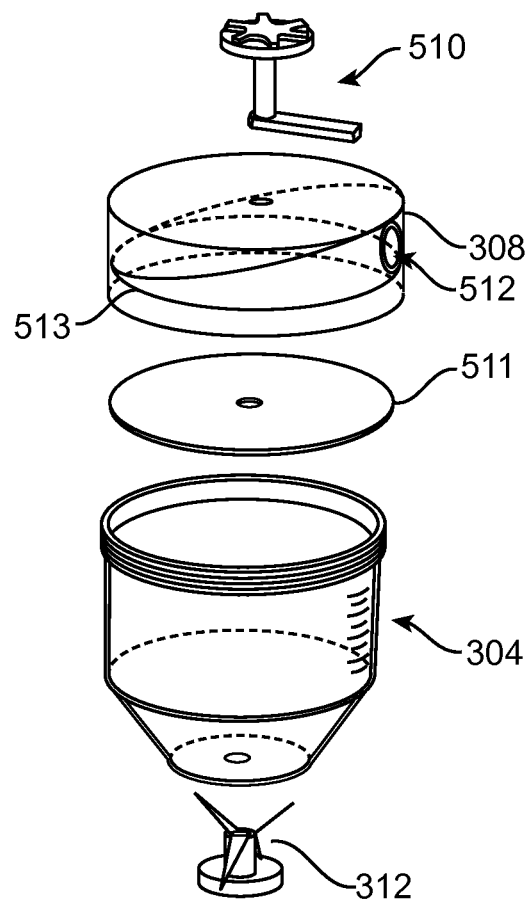
FIG. 5A is an exploded view of a container and cap having a milling feature according to an alternate embodiment.

FIG. 5A is an alternate embodiment of such a method, in which a milling feature 510 is incorporated within the cap 308 to clear the top of the primary filter 511 once the container is inverted and placed to interface with the base station in the same manner as can occur between the agitator 312 and base station (not shown) as described above. In this particular embodiment, the secondary filter 512 is oriented perpendicular to the primary filter 511 and is separated by a curved interior cap 513. Such a design can help further facilitate movement of solution from the primary filter to the secondary and into the nozzle/valve.

Figure 5B:
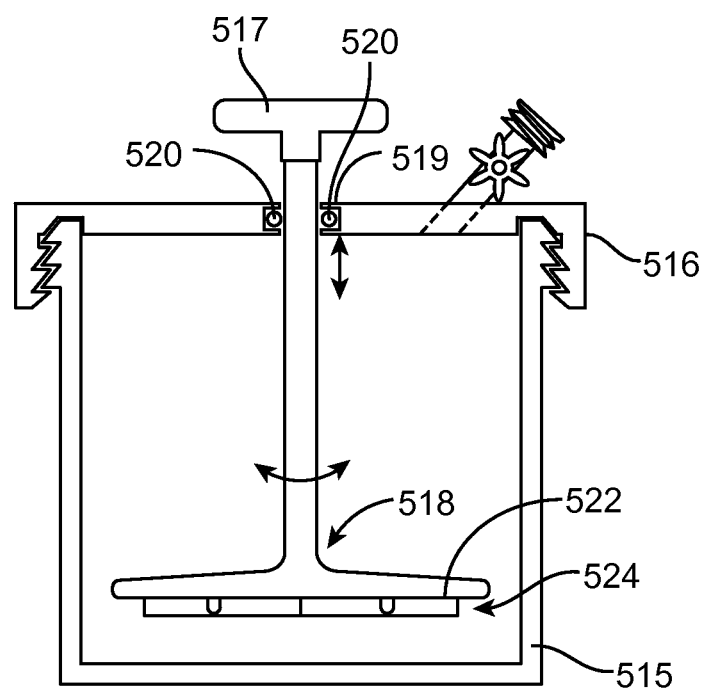
FIG. 5B is a side view of a hand mixing and separation apparatus according to an alternate embodiment.

In further alternative embodiments, other methods for agitation can be incorporated into the cap, container, or other components added in confluence with the closed system. Said alternative agitation methods can include, but are not limited to a hand mixing and separating apparatus. FIG. 5B is a hand mixing and separating apparatus according to an alternate embodiment in which a container 515 has a cap 516 that has a moveable handle 517. The handle 517 is shown in this embodiment as T-shaped but it is expressly contemplated that it can be L-shaped, circular, a knob or any other shape. The handle 517 is mounted to the agitator system 518 via a through-hole 519 in the cap 516 that is sealed with an o-ring 520. The handle 517 which can move along its vertical axis and/or rotate circumferentially in order to actively engage the enclosed solution and initiate homogenization of said solution. The bottom surface 522 of the agitator system 516 is provided with agitation-enhancing structures 524 that promote the homogenization of the stool solution when the handle 517 is vigorously used. Once homogenized, the stool solution can be compressed one last time to provide macro-level separation of any remaining solid masses and fluid within the container, bringing only fluid to the top of the mixture, and the agitator can be locked in place. In other alternative embodiments, such a design can be incorporated with other agitation methods.

Figure 5C:
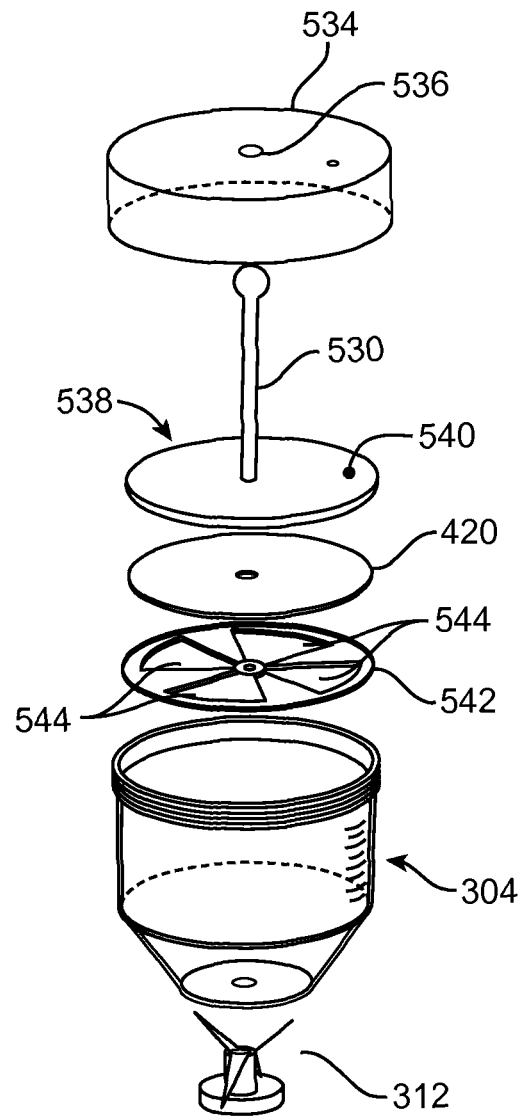
FIG. 5C is an exploded view of a hand mixing and separation apparatus using a plunger according to an alternate embodiment.

FIG. 5C is a plunger filter system that compresses the solution to force it through a primary filter 420. A plunger system includes a handle and handle arm assembly 530 that passes through the cap 534 via a through-hole 536. The handle is attached to a plunger plate 538 that is furnished with an exhaust vent 540. Exhaust vents can also be included elsewhere on the device, and can take the form of a check-valve with low bleed pressure. Charcoal filters or other deodorizing features can be included in such valves to deodorize any air flowing out of the device. The plunger plate 538 is mounted about the primary filter 420 and a guide 542. When the handle arm assembly 530 is pushed, the plunger plate 538 drives the primary filter 420 and guide 542 into the solution, forcing the solution to pass through vents 544 and upwards into the primary filter 420 as the compression of the solution increases. The solution passes through the primary filter 420 and passes through the exhaust vent 540 and collects above the plunger in a filtered state.

Figure 5D:
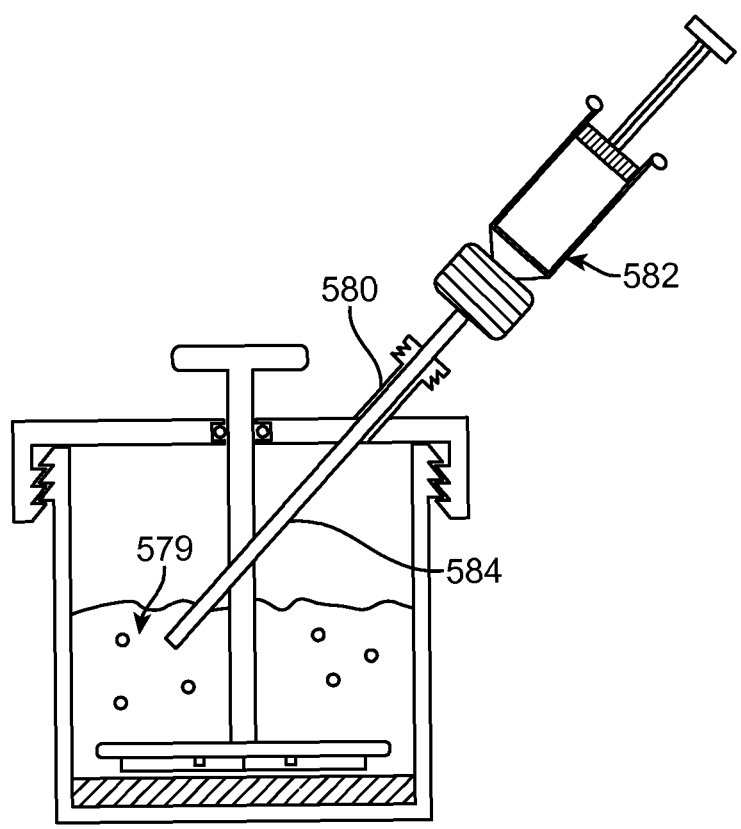
FIG. 5D is a side view of the hand mixing and separation apparatus of FIG. 5B engaged by a syringe with an integral filter system according to an alternate embodiment.

The cap 308 can take various shapes and sizes. It is desirable to make a cap large enough to contain the entire homogenized and filtered sample in an embodiment where the device is inverted so that gravity facilitates filtration, such as in the illustrated embodiment described below in FIG. 8. The cap 308 can also contain sloped walls specifically designed to facilitate the flow of homogenized solution towards the access port, or through subsequent filtrations. The homogenized solution 579 can then be accessed through a luer valve 580, which can or can not include a feature for single or multiple stopcock (including, but not limited to a connection to a standard 3-way stopcock) functionalities (through methods as described above), or with alternative embodiments such as a syringe 582 and a custom, detachable, plastic, non-sharp needle 584, as shown in FIG. 5D. Further filtration can also be included in the plastic needle component, or in a subsequent and final catheter, bag or container utilized for enema delivery, or other delivery methods.

Figure 6:
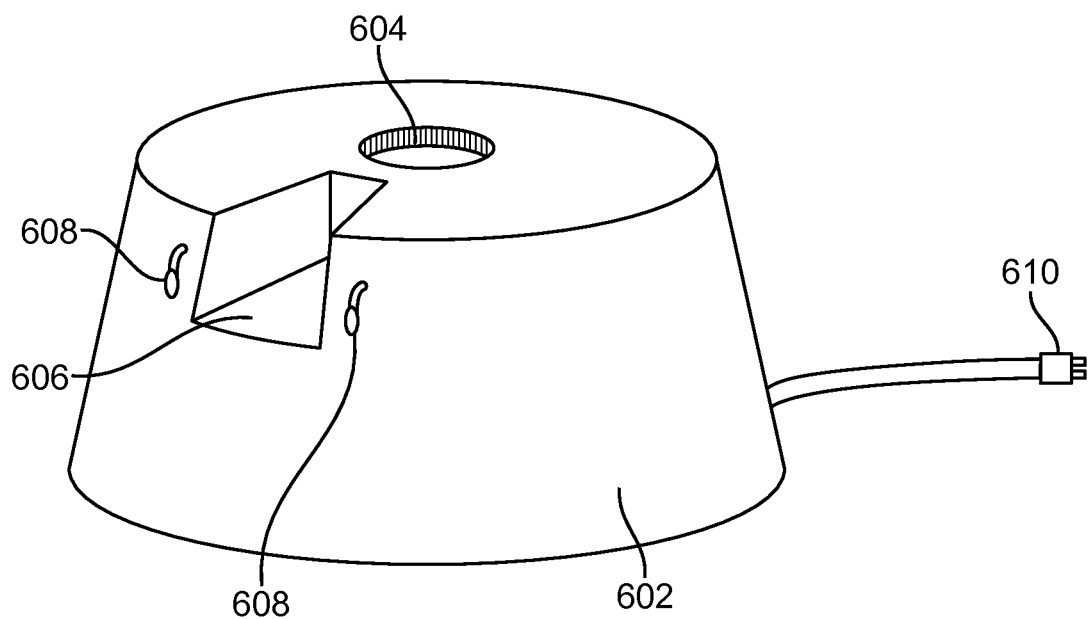
FIG. 6 is an isometric view of the base station according to an illustrative embodiment.

FIG. 6 is an isometric view of an exemplary base station 602 that contains a drive motor 604, the male portion of the gear that interacts with the female portion on the container 404 and the cap 510. As such, in one embodiment, the top of the cap 308 can have a similar shape and configuration to that of the bottom of the container 304, such that both components of the device can interface similarly with the base station, for homogenization and milling arm 510 assisted filtration, respectively. In one embodiment, the bottom of the container 304 and the top of the cap 308 are flat, and designed in such a way that the blending and milling arm features can interface with a base station 602, which resembles a conventionally designed blender. The gear 604 can be designed to make the aligning of the male and female portions easy and intuitive.

Figure 7:
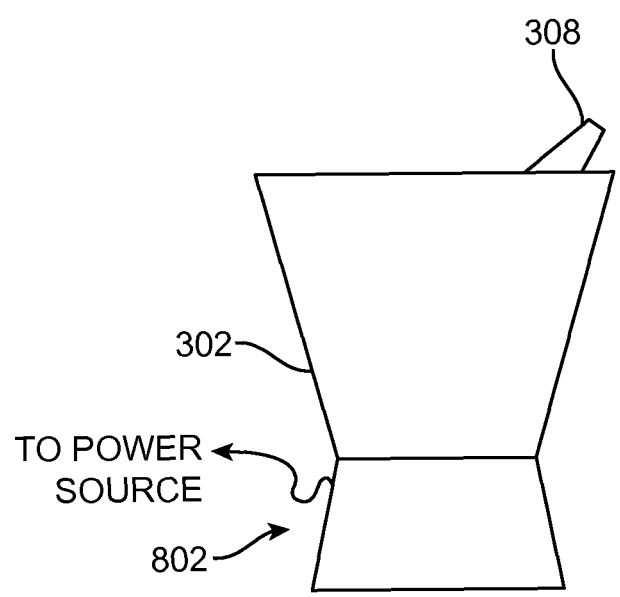
FIG. 7 is a side view illustration demonstrating the interaction between the disposable device and the base station during homogenization according to an illustrative embodiment.

FIG. 7 is a side view illustration demonstrating the interaction between the disposable device 302 and the base station 602 during homogenization according to an illustrative embodiment. The base station 602 can be constructed from a hard disposable plastic. A clearance cavity 606 in the shell of the base station 602 provides a location where the nozzle 308 can reside during the filtration process. A pair of hooks 608 which can be located on the outside of the base station 602 or elsewhere along the body of the apparatus or components added to the apparatus, which can hold an enema bag or other delivery container in place for convenient dispensation of solution through the nozzle 308. Enema bags commonly contain punch out tabs for hanging that maintains the integrity of the seal of the bag, and these hooks can be dimensioned to interact with those tabs. Alternative connections with integral delivery devices can be utilized. Further, connectors such as hooks or tabs can be included on other locations of the device or components coupled to the device to aid in hanging the device from an IV pole to allow for gravity assisted delivery from the device. A plug 610 that can power the illustrated base station 602 with standard 120V AC power. In an embodiment, the base station 602 can be activated with a single power switch and can include a timer as well as speed controls/settings for homogenization and filtration. In an alternate embodiment, the base station 602 can contain an "on button", which drives the motor at one of two different speeds for one of two different lengths of time depending on whether the container 304 or cap 308 is interfacing with the base station. This is accomplished by 2 safety buttons (not shown) on the top of the base station designed to interface with specific male protrusions (not shown) on the container 304 and cap 308, which become depressed when the container or cap is set onto the base station. Such a design ensures that blending and milling are always performed at the correct respective speeds and length of time. In an alternative embodiment, the container with its incorporated agitator will be able to interface directly with various household blenders, thus obviating the need for a novel base station as described above. Alternatively, other adaptive components may be used to allow the container to interface directly with various household blenders.

Figure 8:
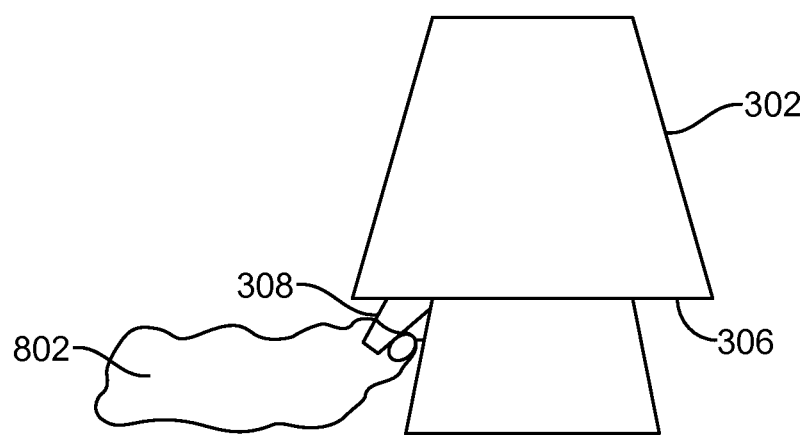
FIG. 8 is a side view illustration demonstrating the dispensation of the filtered, homogenized solution from the disposable device through the nozzle and to an enema bag, or similar delivery container according to an illustrative embodiment.

FIG. 8 is a side view illustration demonstrating the dispensation of the filtered, homogenized solution from the disposable device 302 through the nozzle 308 and to an enema bag, or similar delivery container or device for injection into the receiving patient according to an illustrative embodiment. Once homogenization has occurred the device 302 can be inverted so that the solution will pass through the series of filters 502, 504 within the cap 306. In alternative embodiments, inversion can not be necessary depending on the location of the filters within the closed system, and other methods of applying pressure to the homogenized solution can or can not be utilized. Filtration can be driven by gravity alone, or supplemented by positive or negative pressure induced manually or by a device such as, but not limited to, a vacuum from below, or a syringe, plunger, or compression device from above, acting internally or externally with respect to the closed system or device. The nozzle 308 can be dimensioned to create an air and watertight connection with a variety of delivery containers or devices. Adapters can also be coupled to the nozzle to facilitate said connection. The valve 310 on the nozzle 308 can then be manually activated to allow for the dispensation of the solution from the device 302 to the delivery container or device. Currently available, or customized enema, nasoentereic, or other similar tubes may be attached directly to the nozzle 308 to allow for direct delivery of solution from the container 302 to the receiving patient. Adaptive tubing or other such features may allow the solution to be transferred directly into colonoscopes for delivery into the receiving patient. A feature facilitating metered dispensation of solution can be included on the nozzle, or elsewhere on the device, to provide additional built-in standardization of the fluid volume dispensed. In an alternative embodiment, the dispensation of solution from the device 302 to the delivery container can be achieved by a bladder or bag with a threaded (or other attachment method) opening that corresponds to the same dimensions as the filter apparatus, either at the cap 306 or the base of the container, which can also contain luer valves or other methods of dispensing fluid. The rate of fluid dispensation can be controlled through the valves, and the degree of pressure applied to the system through various methods.

Figure 8A:
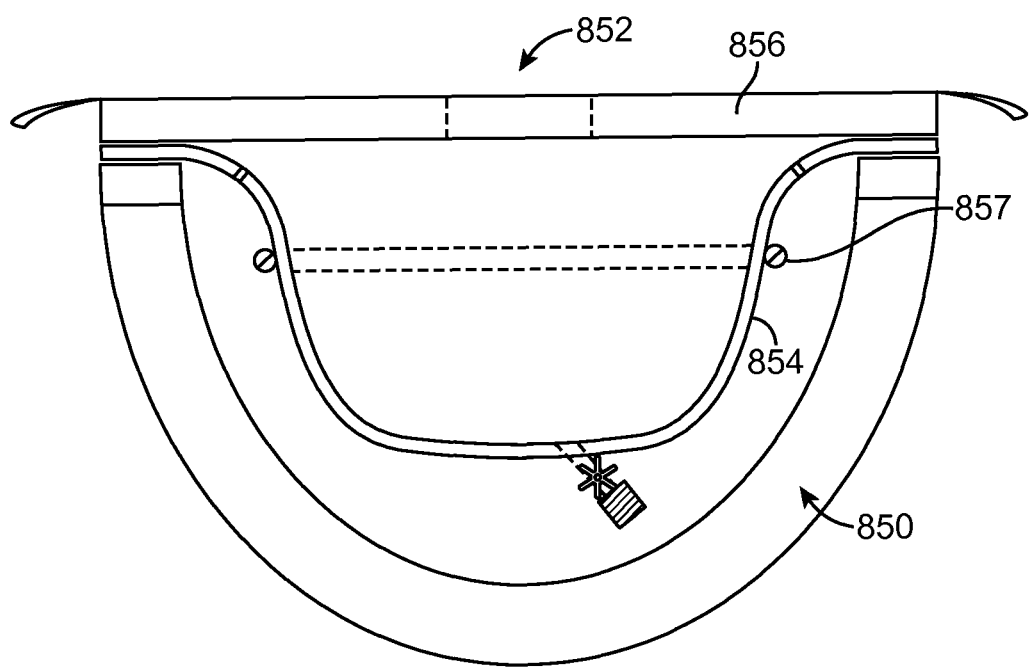
FIG. 8A is a view of a collection bag attachment according to an alternate embodiment.

FIG. 8A is a view of a collection bag attachment to the exemplary toilet 850 according to an alternate embodiment that can be accomplished using separate bracket methods, as mentioned above. The open ends of the bag 854 can incorporate a rigid structure to establish various connections with the bracket for mechanical support. The bag opening 852 can contain a semi-rigid ring 856, or two, preformed half rings 857, to help keep the opening open during stool collection.

Figure 8B:
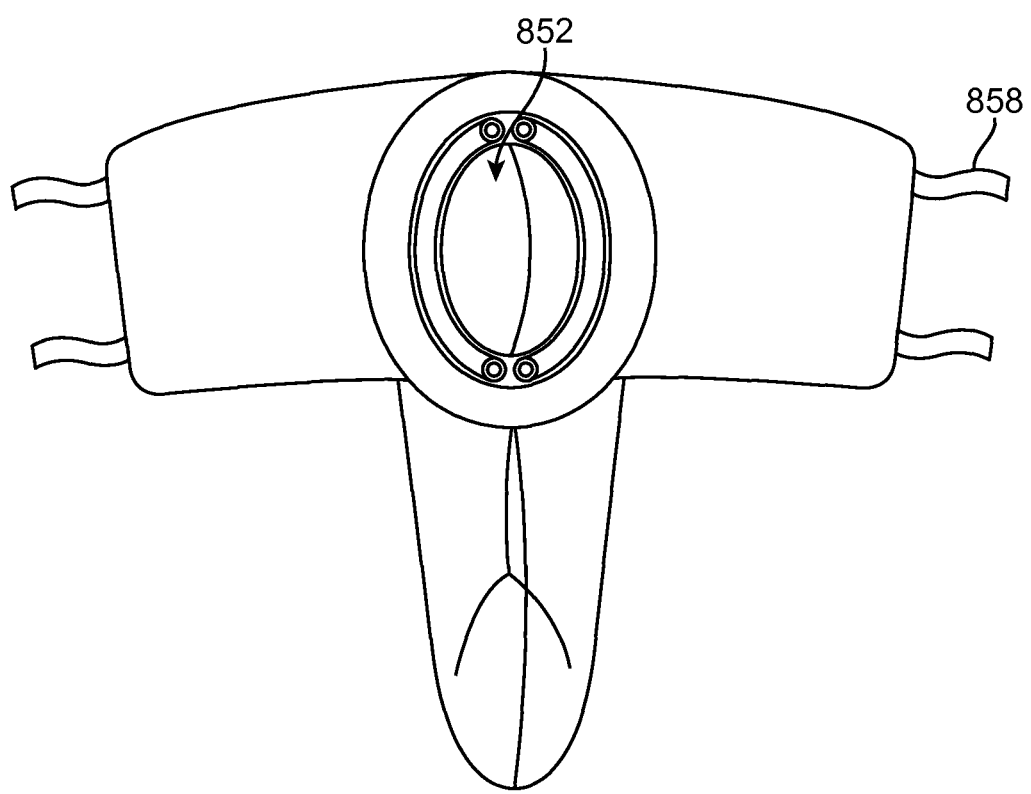
FIG. 8B is a view of a collection bag that does not require a toilet bracket according to an alternate embodiment.

FIG. 8B shows a further alternate embodiment where there is no separate bracket, the open ends of the bag can extend outwards to the sides and attach to the toilet seat (not shown) with heavy-duty tape 858 which can be permanently attached to the bag, or provided separately. The open ends of the bag can be removable from the container via perforations, or other methods if needed for convenience during hanging of the container for gravity enema, or other delivery methods.

Figure 8C:
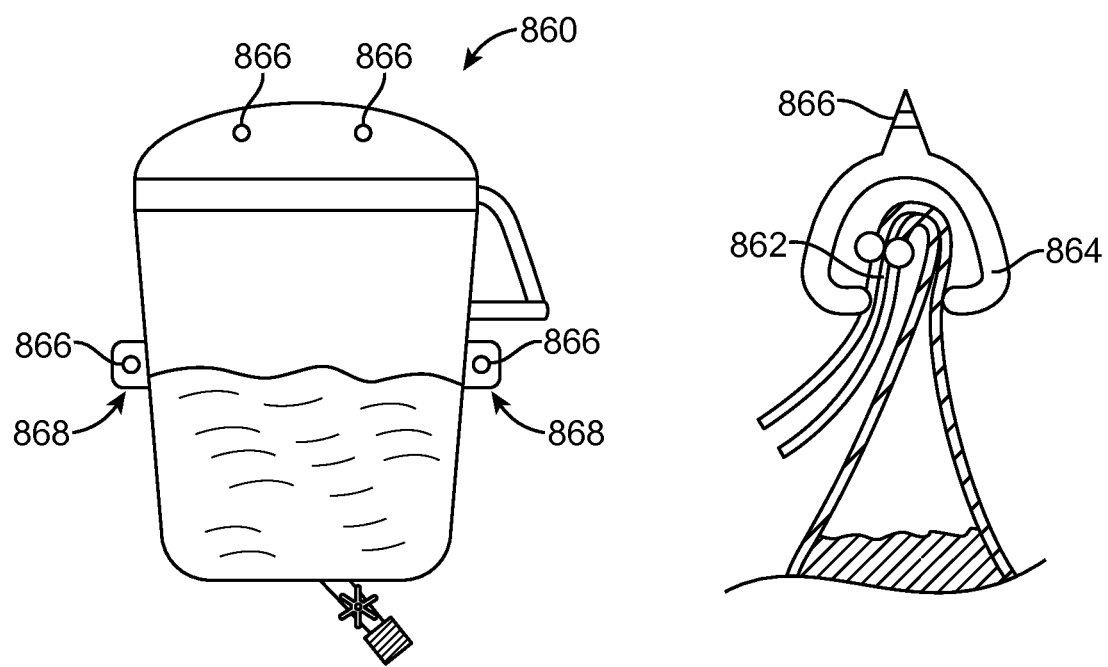
FIG. 8C is a set of views of a collection bag that can be sealed and used as an enema bag according to an alternate embodiment

After stool collection, the bag can be sealed by folding the bag 860 just below its opening 862 by installing or sliding a clip-like component 864 over the folded bag and ring/half ring as set forth in FIG. 8C according to an alternate embodiment. Other sealing methods can include, but are not limited to zippers, snaps, cinches, adhesives, or the addition of components such as a functional cap, as previously described. Again, regardless of the method, once sealed, an air and watertight closed system for processing has been established. Where the seal uses a clip-like component 864, said component can include holes 866 for subsequent hanging of the bag during gravity enema delivery, or other delivery methods. The hanging holes can also be included in tabs 868 on the sides of the bag.

Various agents (as described above) can be added within the closed system through various methods (as described above) including, but not limited to the use of syringe introduction through luer valves, agent-containing compartments built within the bag or added in confluence to the closed system. The luer valve(s) (as previously described) can also be used to facilitate homogenization, subsequent filtration, and rate of dispensation by adding or removing air or liquid via syringe or alternative methods of applying positive or negative pressure can be used.

Figure 8D:
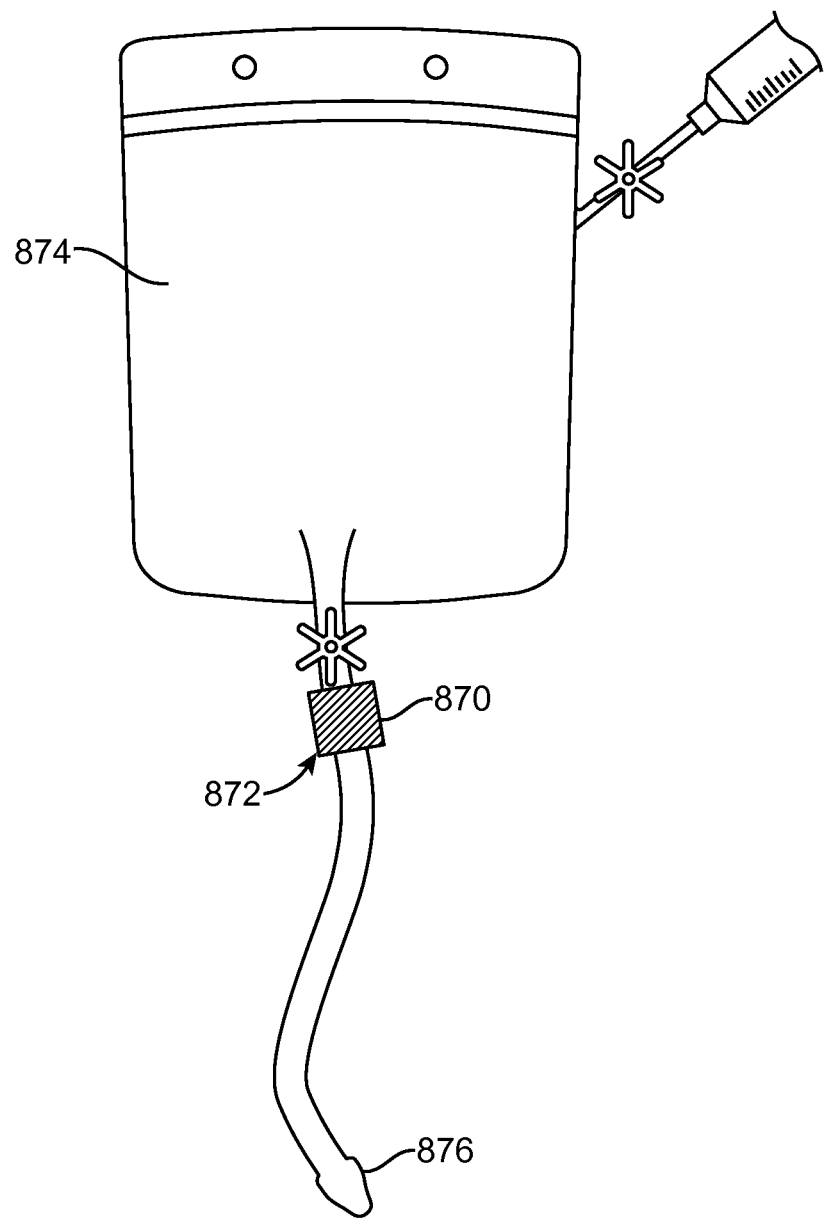
FIG. 8D is a view of a collection bag with an attached catheter system for use in biotherapy according to an alternate embodiment

The bag can also contain said luer valves located elsewhere, such as the sealed end of the bag, to facilitate these functions as set forth in FIG. 8D according to an alternate embodiment. Depending of the intended purpose of the valve(s) 870, the valve(s) 870 can also contain filters 872 capable of separating microflora from homogenized stool, or decontaminating and deodorizing air being evacuated from the bag 874.

Homogenization of stool can be performed manually, or through the use of additional mechanical agitation methods applied to the bag (including those previously described). As such, the bag will be made of such materials and designed in such a way as to maintain functional integrity after considerable mechanical agitation is applied to it. Filtration of homogenized stool will be accomplished through a single filter or multi-stage filters within the bag, valves, caps, catheters, needles, syringes, or other added apparatus incorporated in confluence with this closed system (as previously described). Similarly, as previously described, various methods can be used to aid in the efficiency of filtration. A luer valve 870 at the bottom of the bag 874 (or elsewhere) can then be used for dispensing of liquid directly into various delivery devices. Alternatively, a catheter can be provided with or without a multi-stage filter near the proximal end (or elsewhere along the catheter), and an atraumatic distal tip 876 can be attached to the luer valve 870.

As set forth above in FIGS. 2C, 2D and 2E, any on-toilet embodiment can include removable, rigid or bag-like covers that protect the exposed exterior of the container from contamination, and all components can be disposable.

Figure 8E:
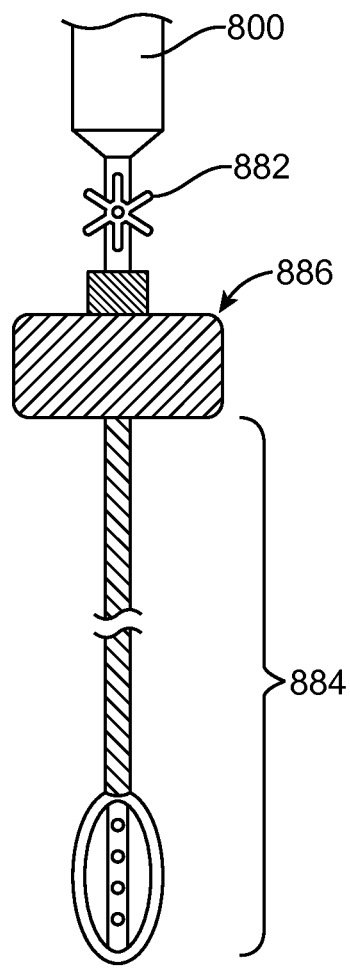
FIG. 8E is a view of the attached catheter system of FIG. 8D according to the alternate embodiment.

FIG. 8E shows an additional alternative embodiment in which the stool collection and homogenization process can be accomplished through direct extraction of stool contents from the donor's large intestine. Saline or other useful agents can be instilled into the donor's large intestine via standard enema methods, or by using a syringe 800, luer valve 882, and detachable instillation catheter assembly 884. The syringe 800 can be either a standard large volume syringe currently in use, or can be custom designed for use with the device set forth herein. In the case of the latter, said syringe 800 can accommodate greater volume (as determined to be optimal) than that of those currently available, can be comprised of at least partially opaque material and contain a filter system 886 composed of a single or multi-stage filters using various methods to aid in the efficiency of filtration, can include previously described methods of introducing various agents or air within its closed system (i.e. additional valves, agent-containing compartments within the syringe or added in confluence etc.), removing agents or air from the system, and can feature a luer valve 882 with various methods for connecting to a catheter 884, including, but not limited to many luer attachable/detachable connections such as a luer taper or luer slip. In an alternative embodiment, the above features can be provided in the catheter component. The syringe 800, luer valve 882, and catheters 884 can also have a rigid or bag-like protective cover (similar to those previously described) that can be removed when desired. The luer-attachable/detachable instillation catheter can have a multi-stage filter 886, atraumatic distal tip, optimized length, and optimized stiffness. If desired, the instilled saline (or other agents) can be allowed to dwell, and/or be extracted and re-instilled multiple times to improve homogenization and microbial harvest, thus requiring only one catheter insertion into the donor.

To prevent intestinal irritation during extraction, the distal tip of the instillation catheter can include a protective feature which prevents suction on the intestinal wall during the negative pressure phase of extraction. Said protective feature can have multiple suction holes separated circumferentially and axially, and one at the end, so as to prevent all of the holes being in contact with the intestinal wall at any one time.

Figure 8F:
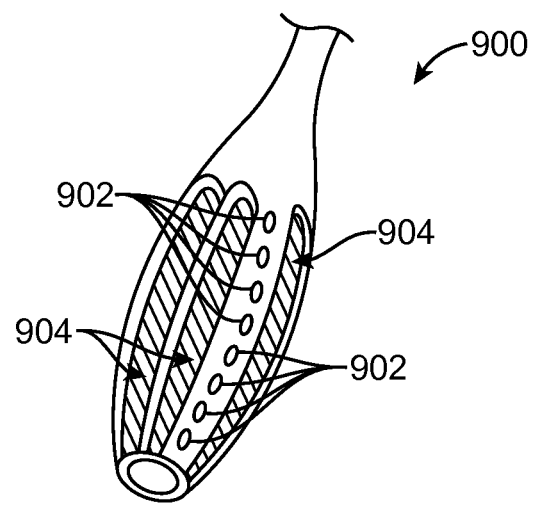
FIG. 8F is a view of the distal tip of the attached catheter system of FIG. 8D according to the alternate embodiment.

FIG. 8F is an alternate embodiment for a protective feature for the distal tip of the catheter. The distal tip 900 can include geometry near the holes' openings 902 that is well rounded and prevents a complete seal between any of the suction holes and the intestinal wall; this includes recessing the holes away from the radial-most surface of the distal tip via ridges or other part geometry. A screen 904 can wrap entirely around the tops of the ridges, which can additionally prevent the intestinal wall from contacting the opening of the holes.

Once an adequate volume of homogenized liquid stool is extracted into the syringe, the instillation catheter can be discarded, and a separate luer-attachable/detachable delivery catheter can be attached to the luer valve on the syringe. In an alternate embodiment, the instillation catheter, delivery catheter and syringe are connected with an adapter such as a 3-way stopcock (or other such component) allowing redirected, and unidirectional flow, such that the extracted homogenized stool solution can be immediately delivered directly from the donor to the recipient within one closed system device. Said delivery catheter can contain a multi-stage filter, optimized length, optimized stiffness, and an atraumatic distal tip, to allow for enema delivery of the extracted liquid within the syringe to the target recipient. Alternatively, when desired, said delivery catheter can be of a smaller size and feature a tip designed to connect directly with other delivery devices.

In addition to the components and embodiments of the device as previously described, the device can include additional adaptive components allowing the microflora to be transferred within the closed system into subsequent components or apparatuses used to facilitate further refinement, processing, isolation, or analysis of the fluid and its contents for subsequent use in a wide variety of applications, including, but not limited to delivery methods and analytic processes. Such additional components (as described below) can facilitate discrete applications of the contents processed by the device(s), including, but not limited to optimized isolated microflora for consumption by mouth or utilization for a vast range of analytic purposes as described above. Such consumable applications can include but are not limited to various methods of encapsulation and enteric-coating of the microflora, or integrating the microflora into other consumables such as drinks, yogurts, gelatin products, puddings, ice creams, candies, or other similar products. Such methods can require refining microflora in a variety of ways including, but not limited to full extraction out of solution, with or without the subsequent addition of various agents and collection and storage in and/or dispensation from a variety of specialized containers.

Figure 9A:
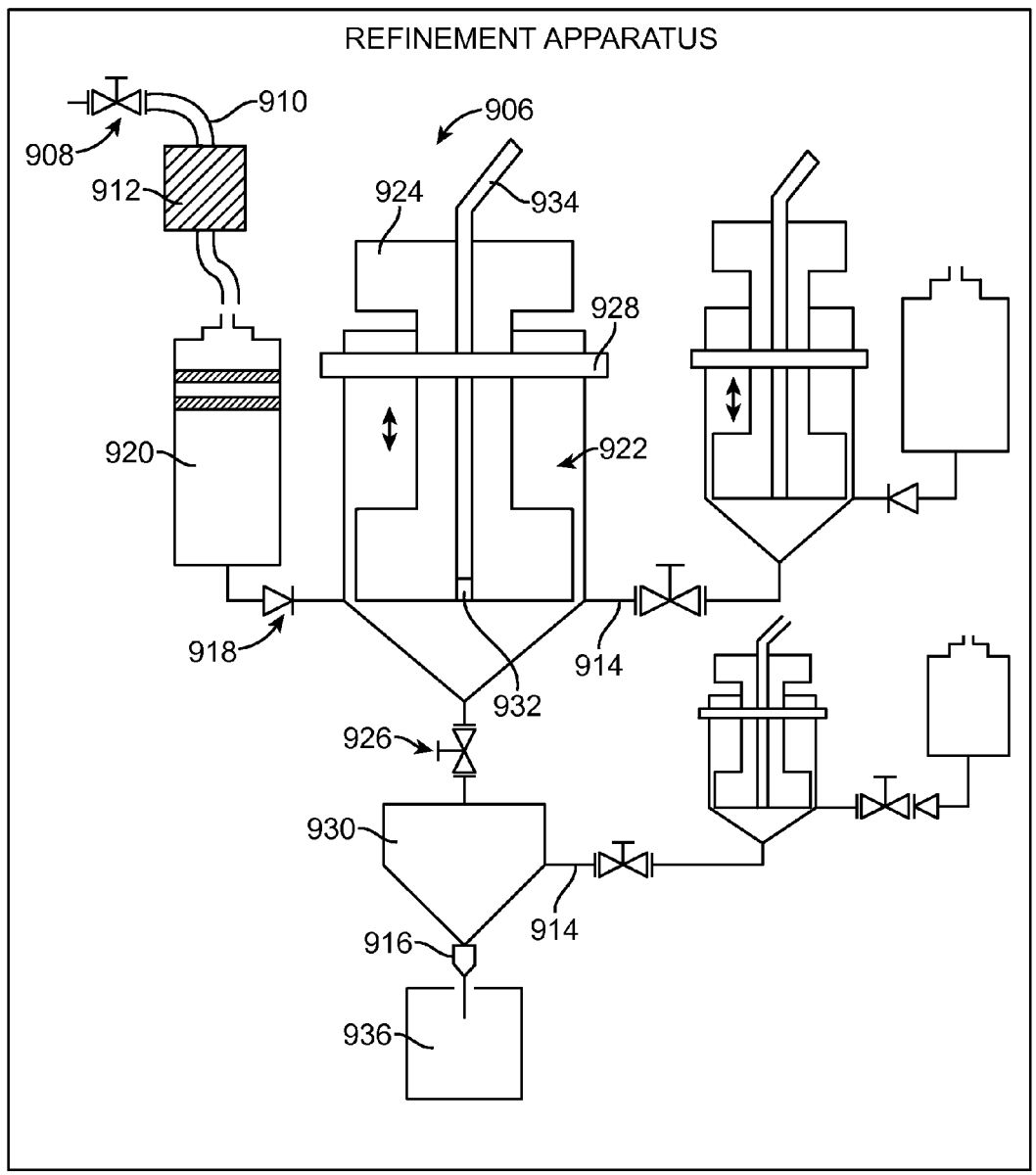
FIG. 9A is a schematic view of a refinement apparatus according to the alternate embodiment.

FIGS. 9A to 9D are a series of embodiments for refinement apparatuses. FIG. 9A shows an embodiment of a refinement apparatus 906 the features of which can include, but are not limited to a flexible or rigid tube, where one end connects to a luer valve on the primary device 908, or to a luer valve at one end of a flexible or rigid intermediary tube 910, while said tube connects to the primary device with another luer valve. The apparatus 906 can include integrated and interchangeable filters 912, inlet/outlet ports 914 for adding or removing desired or undesired substances, a mechanism for adjustable metered closed-system dispensation or removal of substances (described below) through single or multiple dispensing ports 916, which connect to a variety of subsequent components for various applications (therapeutics and analytics). An illustrated embodiment of a mechanism for adjustable, metered closed-system dispensation or removal can include, but is not limited to, one with a check valve 918 that separates a reservoir 920 from a dispensing lumen 922, or plurality of check valves and dispensing lumens from a reservoir 920, a movable plunger 924 that seals to the inside surface of a dispensing lumen 922, and a second valve 926 (for example, a check valve, luer valve, or any other useful valve known to the art) at the end of the lumen. The maximum fillable volume of the dispensing lumen is adjusted by the user via a mechanism such as a lockable slide 928 or other such mechanism, and is filled with the contents of the reservoir 920 by actuating a plunger 924, whereby the plunger movement increases the fillable volume of the dispensing lumen 922 up to the maximum fillable volume by creating reduced pressure within the dispensing lumen causing the contents in the reservoir to flow into the dispensing lumen through the check valve 918.

Reverse actuation of the plunger 924 closes the check valve 918 and opens the second valve 926 (depending on the valve type), dispensing the contents out of the dispensing lumen 922 into a secondary compartment 930, which can be optionally incorporated within, or removably attached to the dispensing lumen 922 depending on the embodiment. In alternate embodiments the functionality of the plunger 924 can be replaced with other methods of producing this force, including, but not limited to the use of positive and negative producing air or gas pumps, vacuums, or other methods known to the art. In addition, the mechanism by which this feature is operated can include, but is not limited to, manual manipulation, the use of weights, a variety of automated mechanism, or other useful methods known to the art. Such an embodiment of the refinement apparatus can include the dispensation of microfloral solution through ports 926 and 916 into additional apparatuses for further refinement and isolation of microflora or other components, for direct or subsequent use for therapeutic or analytic purposes.

In addition to the features described above, the refinement apparatus 906, can include additional adaptive components that can be coupled directly to any of the various primary device embodiments, or to other subsequent apparatuses described below. Said additional components can or can not include additional multi-staged filters or access ports as previously described. In such an embodiment, the primary mode of microflora isolation features a filter 932 or a multiplicity of filters (similar or different to those previously described including, but not limited to those such as borosilicate microfiber or other functionally similar filters known to the art) which allow the passage of fluids, but not microflora. The filter 932 can be located anywhere within the apparatus or those coupled to it, and can be easily interchanged with other filtering or non-filtering materials through external mechanisms.

In the illustrated embodiment, said filter 932 is included at the head of the plunger 924. Actuating the plunger 924 downward forces microflora downwards below the filter 932 at the plunger head and can help facilitate movement of microflora out of the dispensing lumen 922 through the second valve 926 into the secondary compartment 930 and eventually into any number of subsequent compartment(s) (as set forth below) and microflora-deprived fluid upwards through the filter 932 on the plunger head. In alternative embodiments, a filter is placed below the plunger and the plunger can or can not contain a plunger filter, and can serve to force fluid downward through the lower filter while retaining the microflora on that filter's surface. In addition, not only can the filter be interchangeable, there can be other features serving to inhibit the filtering ability of the filter if so desired to manipulate the pressure gradients within the lumen. Such methods can include, but are not limited to, covering and uncovering the filter with a nonfiltering material by twisting the handle of the plunger or other methods known to the art. Unwanted fluid collected above the filter 932 can then be removed via a syringe or other methods through an access port 934 positioned within the plunger 924 or elsewhere within the compartment housing the plunger. In an additional embodiment, the unwanted fluid can be removed from the microflora solution through a negative pressure port, with microflora retained within the apparatus by applying a hydrostatic pressure, electromagnetic radiation, electrostatic force, electrochemical force, centrifugal force (or other useful methods known to the art) to the solution. Additional access ports 914 (including luer valves, 3-way stopcocks, metered dosing systems and/or others known to the art) below the plunger 924 can or can not be used to allow for the isolated microflora to be further processed within the refinement apparatus 906, or to transfer the microflora into a subsequent container apparatus 936 (as described below) for processing, storage or direct applications previously described above or below. Depending on the selected embodiment, microflora can be stored within the refinement apparatus 906 or other components with or without a feature allowing the microflora containing compartment(s) below to be removed (though a variety of mechanisms).

In the circumstance where isolated refined microflora and/or other desired contents are to be consumed orally, either directly, through encapsulation, or through incorporation with other consumable agents. To prepare the microflora for consumption, various agents can be added to the isolated microflora through access ports 914 within the refinement apparatus 906, and/or the microflora can be transferred to subsequent components prior to or after the addition of said agents, and the microflora can or can not be subjected to various processes including, but not limited to such processes as freeze-drying or other preparatory methods within the isolation apparatus or in subsequent components. Similar such methods can be used in the case that the microflora or other contents are to be used for analytic or other purposes.

Figure 9B:
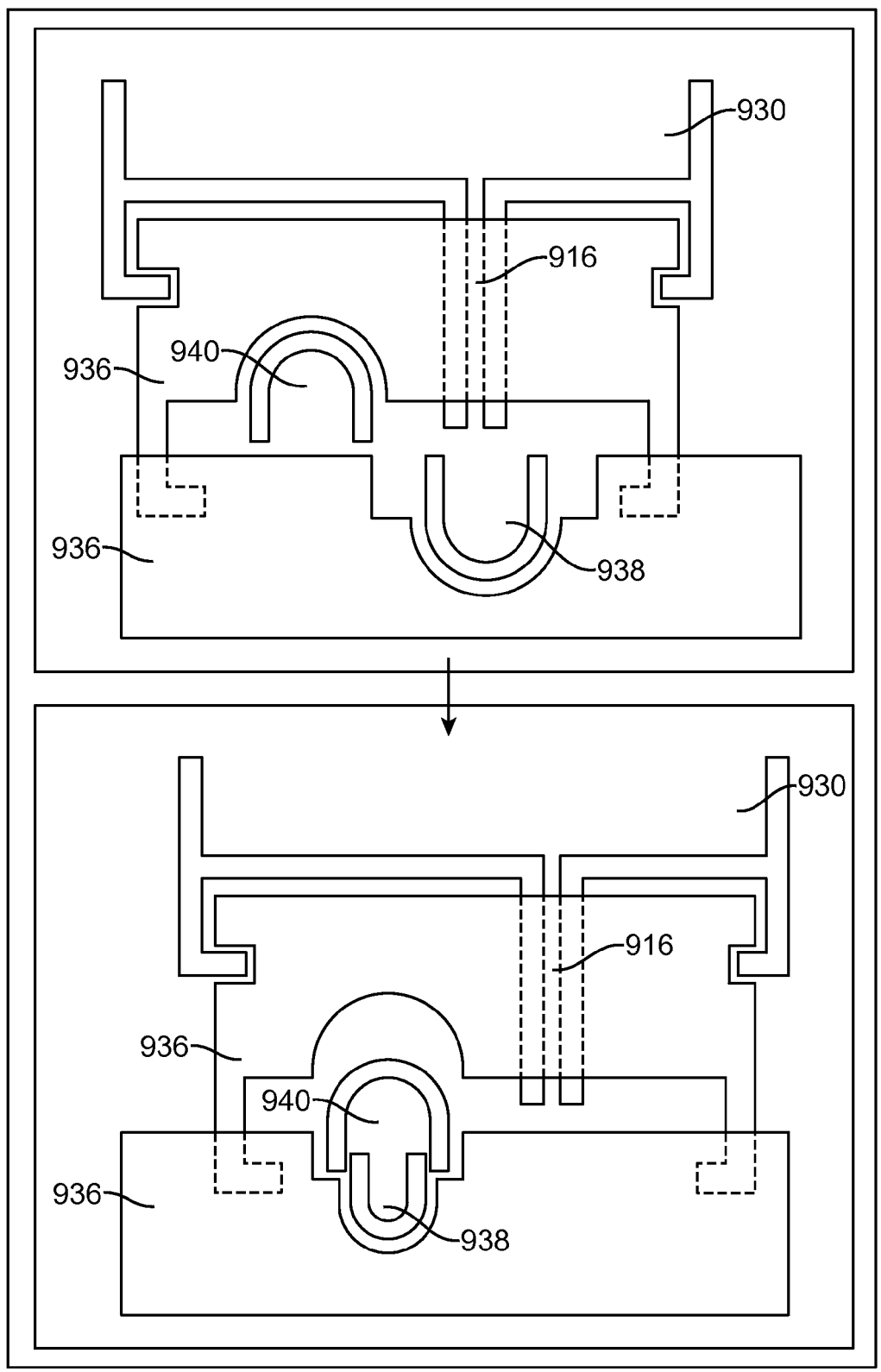
FIG. 9B is a schematic view of a refinement apparatus having a container apparatus according to the alternate embodiment.

FIG. 9B shows an exemplary embodiment, where the refinement apparatus can include or adapts to a container apparatus 936, which can or can not resemble a tray with any number and type of empty container units 938. The container apparatus 936 can be included within the refinement apparatus 906, or adapted to it through a variety of methods. In one embodiment, the container units 938 can be empty capsules (bottom halves of the capsules without the complementary lid halves), where the isolated and prepared (per the selected method respective to the capsule type) microflora can be dispensed through a variety of potential methods and collected within said capsules. A complementary tray of corresponding container lids 940 (depicted in this embodiment as capsule lids) can be pressed down or otherwise attached to close the capsules. An exemplary tray of capsule lids can be included in various components of the apparatus or separately, and the mechanism by which the container lids 940 are attached to the container units 938 can be accomplished through a variety of methods, including, but not limited to, manual manipulation, various automated methods, or other useful methods known to the art. The container apparatus 936 and units 938 can then be removed from the refinement apparatus, and the container units 938 removed from the container apparatus 936 to be used for a variety of purposes. In alternative embodiments where the microflora is to be consumed as a food (such as a gelatin or yogurt based product, or any other similar product) or drink rather than a capsule, similar methods can be used as those described above, but where the container apparatus 936 is comprised of container units 938 resembling moulds (using various moulds, variety of shapes, colors, materials and lid closure designs), and specialized container lids 940 are used to create a wide variety of closed container units 938 either as included within the refinement apparatus 906 or separately, as described above. The container components can be made of such materials as to allow for durable storage at standard temperatures used to preserve microflora or other desired contents, and to withstand dry-freezing, and/or sterilization procedures, among other processes.

Figure 9C:
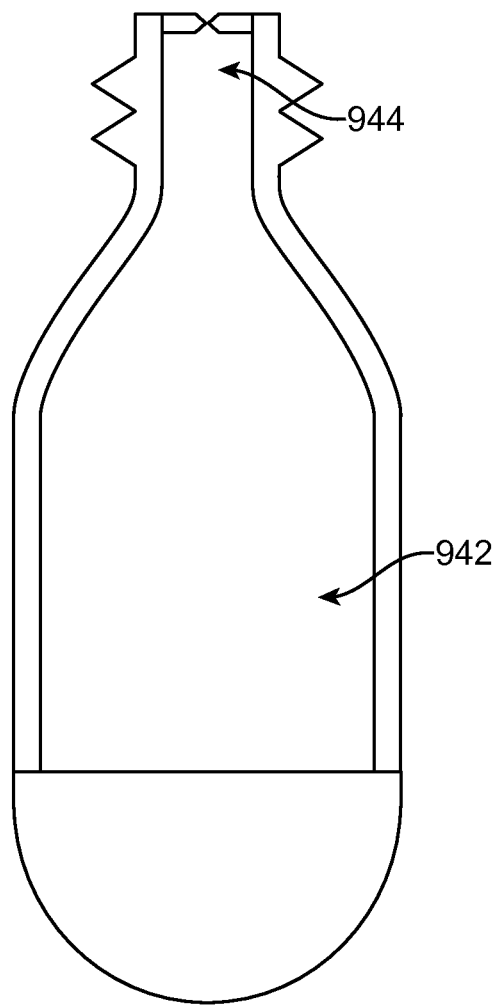
FIG. 9C is a view of an illustrative specialized subsequent container apparatus according to the alternate embodiment.

Depending on the use, the contents of the containers units 938 can be immediately consumed, or stored for later use. The container units 938 can also include features for assessing the amount of contents within (such as volume line indicators) and/or to confirm that a desired product(s) is present or undesired product(s) is absent (using such analytics as those described above). FIG. 9C shows an additional embodiment of a container unit 938 which can be provided with features allowing for closed system dispensation of its contents including, but not limited to a design functionally resembling a liquid dropper 942 (such as those currently used for oral liquid medications, eye drops etc.), where fluid is dispensed through a port 944 in the container unit 938 which only opens upon squeezing it, and then closes when pressure is released.

Figure 9D:
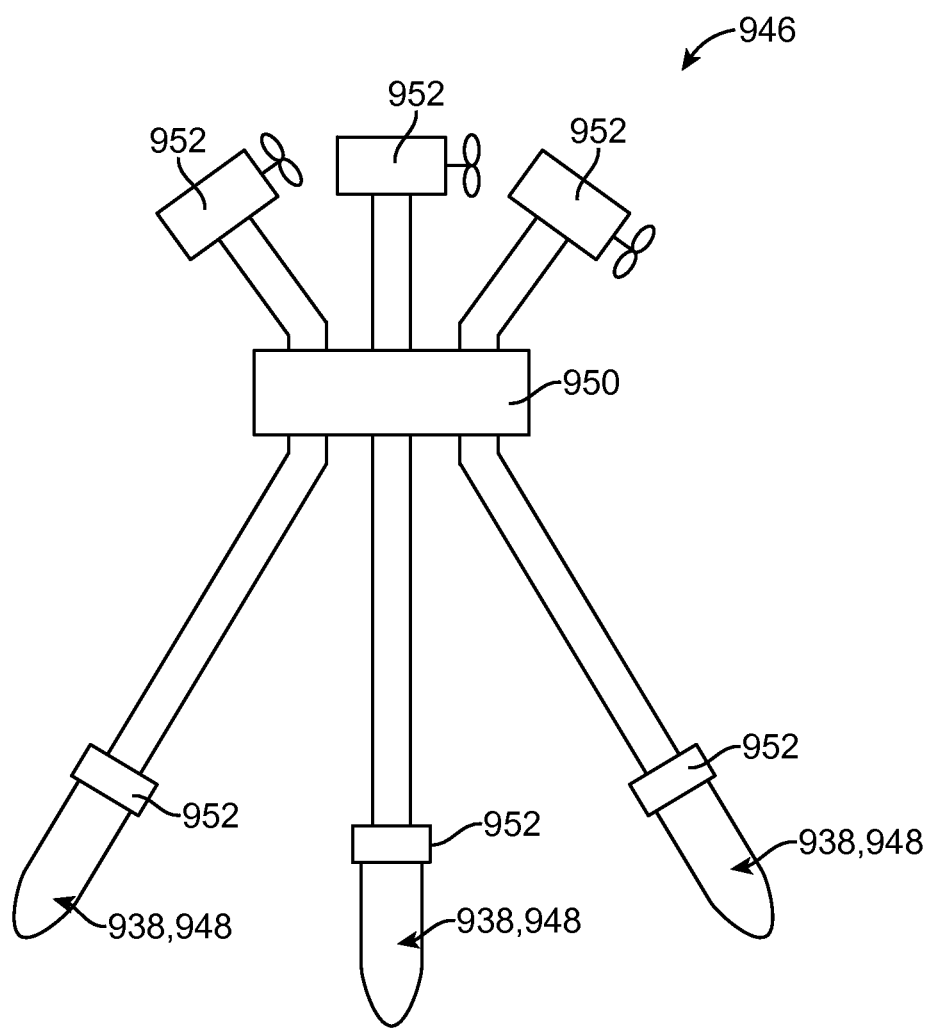
FIG. 9D is an exemplary centrifugal array of containers according to the alternate embodiment.

FIG. 9D shows an additional embodiment of a specialized subsequent container apparatus 936, which is designed as a centrifuge vial apparatus 946 which can be desirable to adapt to embodiments of the primary device nozzle 308, refinement apparatus 906, or potentially any of the devices or apparatuses described above to facilitate further refinement and isolation of microflora or other contents. Said centrifuge vial apparatus 946, can contain any number of adapted container units 938 designed as specialized centrifuge vials 948. It can include a rotary feature 950 which enables the centrifuge vial apparatus 946 to rotate 360 degrees in a horizontal plane where it interfaces with any other device or apparatus described above, allowing the centrifuge vial apparatus 946 to remain attached to said connected other components during centrifugation. The centrifuge vial apparatus 946 can include a specialized centrifuge vial lid(s) 952 (which can or can not resemble other container lid(s) 940 as described above) which automatically close upon being removed from its connection with other apparatuses, or remain open for creation of an open-system. The vial lid(s) 952 can be located on a single aspect of the centrifuge vial apparatus 946 and/or incorporated in each individual vials 948.

The lid(s) 952 can be comprised of an elastomeric, self-healing film that can be punctured by dispensing lumens 916 (incorporated as primary components of the centrifuge vial apparatus 946, other components of the refinement apparatus 906, or other apparatus), and automatically seal when not punctured, or comprised of other lid closure known to the art. The centrifuge vials could house a vial liner which can be removed from the vials to serve as a container, avoiding contamination of the vials themselves. The centrifuge vial apparatus 946 can be fitted for a variety of centrifuge models, or vial sizing adapters can be used to enable the centrifuge vial apparatus to be used with most centrifuges. Prior or subsequent to centrifugation, access ports 914 and 916 within the refinement apparatus 906, centrifuge vial apparatus 946 or as incorporated within the connection apparatus or other such coupled components, can be used for metered or non-metered addition or removal of solid, liquid, or gaseous matter into or out of the apparatus. Subsequent to centrifugation, and separation of microflora, supernatant can be removed through the use of the aforementioned features, and directly disposed of while still retained within a closed system. The centrifuge vials 948 within the apparatus can be removable from the vial apparatus 946 through a variety of methods, which allow the vials 948 to remain closed, having never exposed their contents to the environment. Such a mechanism can be the same or different from that used for the container units 938 as described above.

The centrifuge vial apparatus 946 and/or centrifuge vials 948 can include a variety of features allowing the contents contained within to be accessed, stored, or dispensed and utilized. Such features can include, but are not limited to, luer vales located anywhere on the individual or combined components, elastomeric lids as described above, standard screw, twist or snap (or other methods known to the art) caps located on either or both sides of the centrifuge vial apparatus 946 and/or individual vials 948 and which can also include the elastomeric lid as previously described. In alternative embodiments, the vials 948 are designed to functionally resemble a liquid dropper 942 (such as those currently used for oral liquid medications, eye drops etc.), where fluid is dispensed through a port 944 in the vial which only opens upon squeezing the vial, and then closes when pressure is released. The centrifuge vial apparatus 946 and/or individual vials 948 can be made of opaque, translucent, or colored material, and can contain external volume indicators, and can also be made of such materials as to allow for durable storage at standard temperatures used to preserve microflora or other contents, and to withstand dry-freezing, and/or sterilization procedures, among other processes.

Figure 10A:
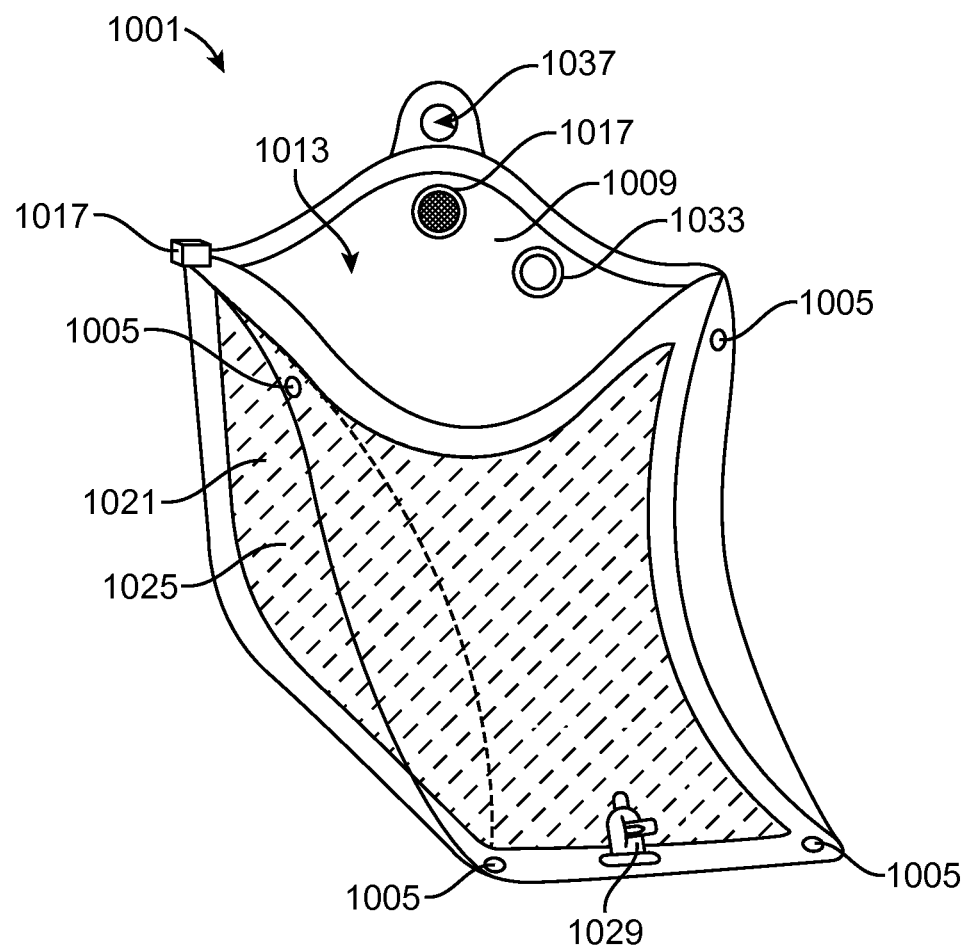
FIGS. 10A to 10E are isometric views of a stool collection and filtration bag in use according to various embodiments.

FIGS. 10A to 10E are isometric views of a stool collection and filtration bag 1001 in use according to various embodiments. FIG. 10A shows the stool collection and filtration bag 1001 in an open configuration. The bag 1001 is flexible and may be made of an expandable material such that it can accommodate various volumes of stool and solvent. The bag 1001 can be opaque to provide a less offensive look and feel to the user but may be at least partially transparent, for example, by having a transparent strip, so that the volume of the bag 1001 contents can be tracked. The bag 1001 comprises brackets 1005 disposed on the edges, typically the corners, of the bag. These brackets 1005 can facilitate coupling of the bag 1001 to the toilet brackets described above so that the open bag 1001 can collect stool while a donor is defecating when seated on a toilet seat and later removal from the toilet seat. The brackets 1005 may also be used to facilitate the folding or rolling of the bag 1001. The bag 1001 can open to a stool collection compartment 1013 through opening 1009. The bag 1001 can be closed by sliding a sliding mechanism 1017, or through other sealing methods. The bag 1001 comprises a closeable deodorizing filter 1017 which leads to the stool collection compartment 1013 so as to ventilate the contents of the compartment 1013 if desired. The bag 1001 further comprises a filter 1021 which is typically flexible and separates the bag 1001 into the stool collection compartment 1013 and one or more filtrate compartments 1025. The filter 1021 may comprise one or more filter sheets so as to form a "multi-filter" system much like those described above. In many cases, the filter sheets may have different pore sizes as described above. For example, the filter sheet closest to the stool collection compartment may have larger pore sizes, for example up to 4,000 μm or 2,000 μm to filter out most solids, while the filter sheet closest the filtrate compartment has a smaller pore size, for example of at least 0.22 μm or at least about 0.44 μm to only let bacteria and other microflora through, to minimize clogging of the smaller pores of the latter sheet. The filtrate compartment 1025 may open to a dispensing valve 1029 of the bag 1001 which may be a luer valve. The bag 1001 may further comprise a resealable access port 1033 which may lead into either the collection compartment 1013 or the filtrate compartment 1025. The access port 1033 may be used, for example, to introduce a solvent, gases, or other matter into the bag 1001 or to extract a sample of stool or stool and solvent mixture from the bag 1001, for example, by using a pipette. The bag 1001 may further comprise a hanger tab 1037 to facilitate the hanging of the bag 1001 for a variety of purposes such as storage, weighing, direct delivery via enema or nosoenteric tube, or hanging as to facilitate filtration by gravity.

Figure 10B:
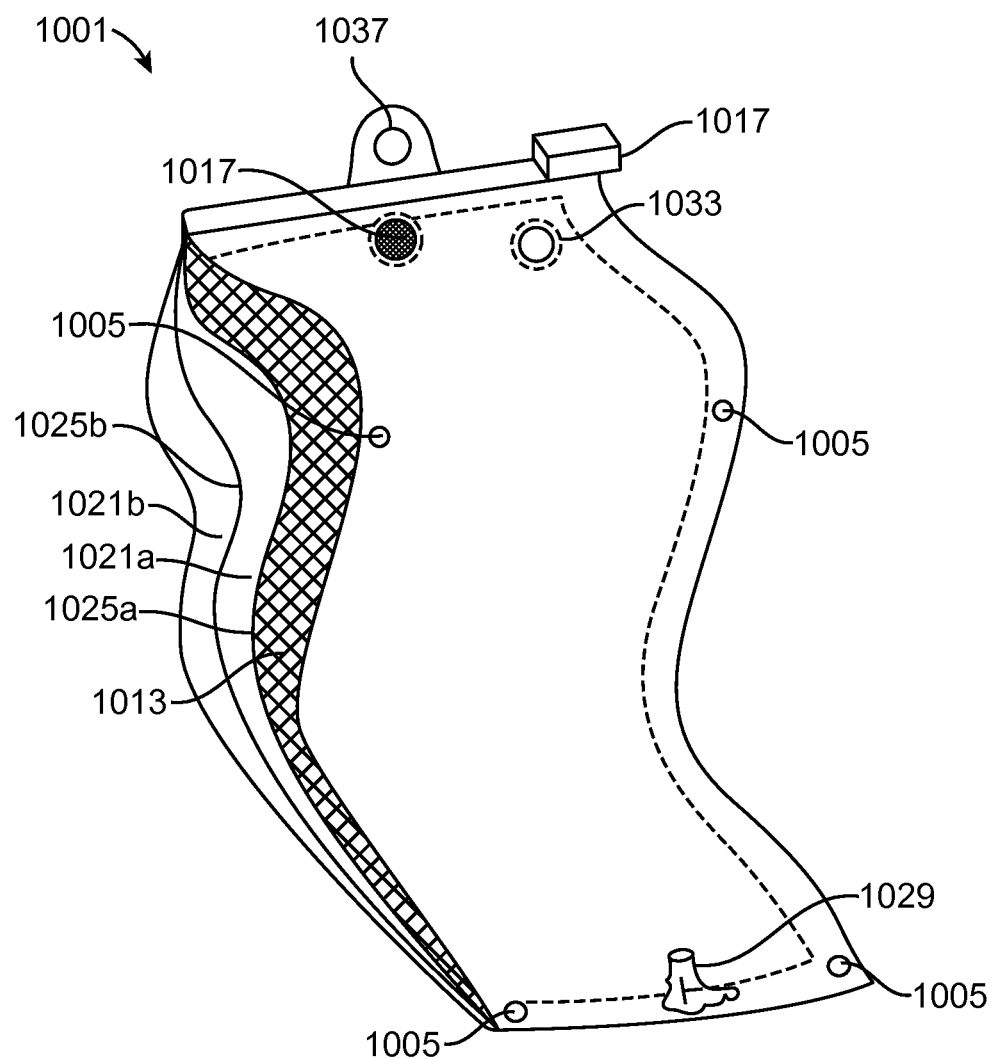

Once stool is collected by the bag 1001, the bag 1001 is removed from the toilet seat and may be closed by sliding over the sliding mechanism 1017 as shown in FIG. 10B. This may place the contents of the bag 1001 in an anaerobic, closed environment. In some embodiments, for example as shown in FIG. 10B, the bag 1001 may comprise two or more filtrate compartments such as compartments 1021a and 1021b, separated by filters 1025a and 1025b. Filter 1025b may have a smaller pore size than filter 1025a as described above.

Figure 10C:
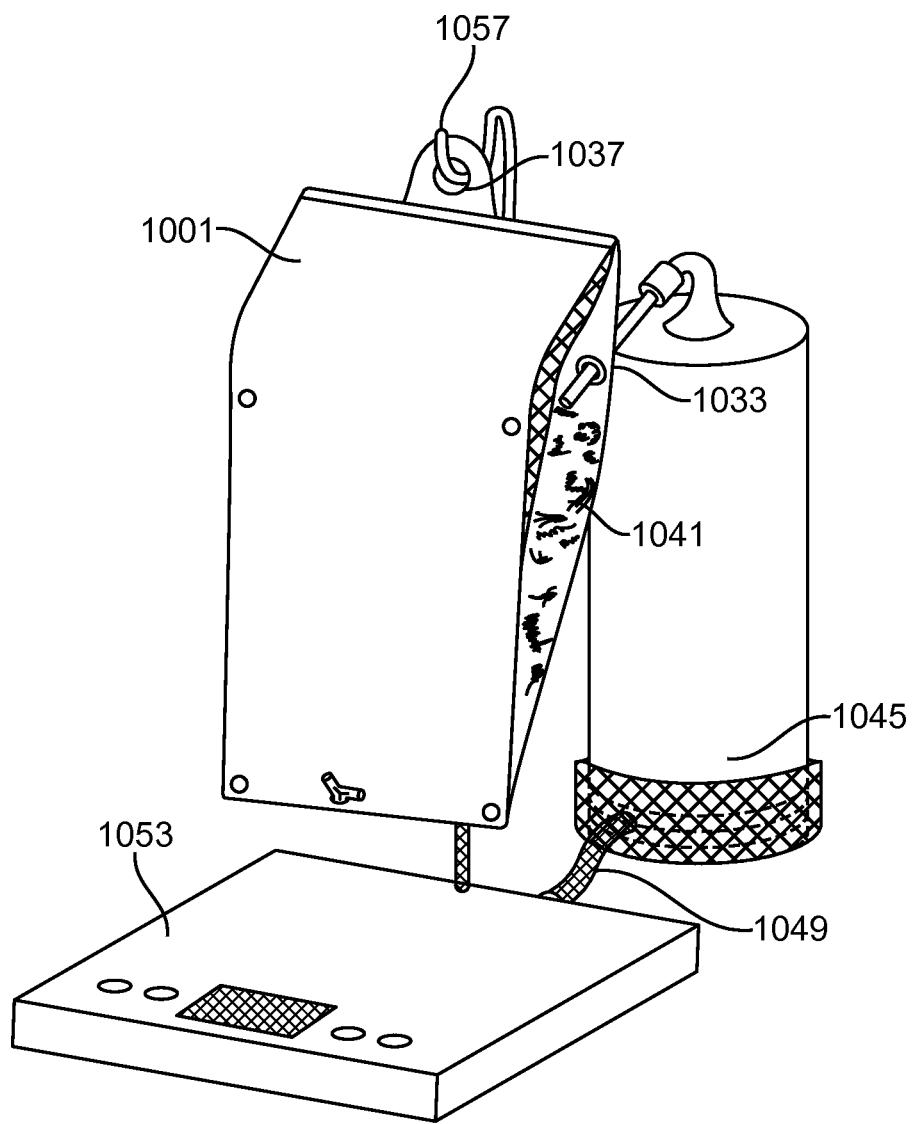

Once stool is collected by bag 1001 and the bag 1001 sealed to place the collected stool in a closed environment, saline or other sterile solvent can be added into the bag, for example, as shown in FIG. 10C. The volume of saline added to the collected stool may be dependent on the weight of the collected stool. As shown in FIG. 10C, a scale 1053 may be used to determine the weight of the collected stool. The scale 1053 may comprise a hanger 1057 that couples to the hanger tab 1037 of the bag 1001. The weight of the bag 1001 will typically be predetermined and known and the weight of the stool can be determined based on this known bag weight. The volume of solvent or other saline added to the collected stool may be based on the weight of the stool. For example, the amount of solvent can be added such that the resulting mixture of stool and solvent will have a desired, uniform density that will be the same for any stool donor. Having a uniform density for any homogenized mixture may be helpful for quality control purposes, especially where stool is collected from many different donors to develop a bank or repository of various microflora, or where regulatory guidelines require standardized densities to ensure efficacy and safety. Also, the volume of solvent or other saline may be added such that the later filtrate will have a predetermined concentration of microflora. A weight-based algorithm, for example as described above, may also be used to determine the volume of saline or other solvent to provide to the collected stool. A saline reservoir or pump 1045 can be connected to the scale 1053 via data connection 1049 so that an appropriate volume of saline can be pumped into the bag 1001 through access port 1033. For example, 500 milliliters of saline for every 50 g of stool, or other varying ratios of saline up to possibly 2 liters or more for every 30 g or less of stool may be provided.

Figure 10D:
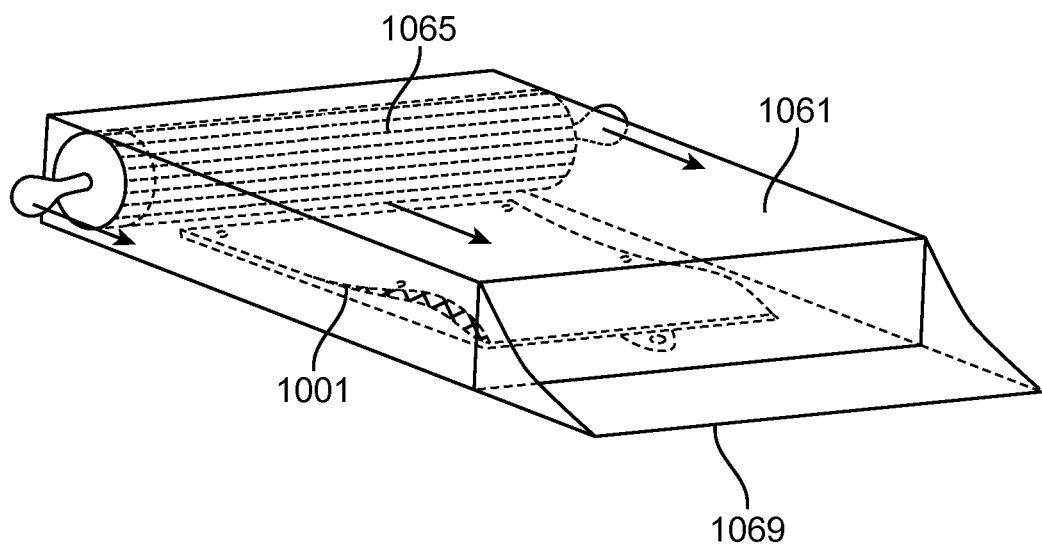

With the collected stool combined with saline or other solvent in the closed environment of the bag 1001, the collected stool and solvent is then homogenized. Embodiments of the invention provide various means for homogenization such as a paddle blender (commercially available, for example, through Seward Limited of Great Britain), a roller mechanism, a mashing mechanism, or other means of applying external physical force to the bag 1001 to break apart the collected stool. As shown in FIG. 10D, the bag 1001 may be placed into a roller mechanism 1061 comprising a moveable rolling pin 1065 and a door 1069. To homogenize the collected stool and solvent within the bag 1001, the bag 1001 can be placed within the roller mechanism 1061, the door 1069 is closed, and the rolling pin 1065 is actuated to mash the contents of the bag 1001.

Figure 10E:
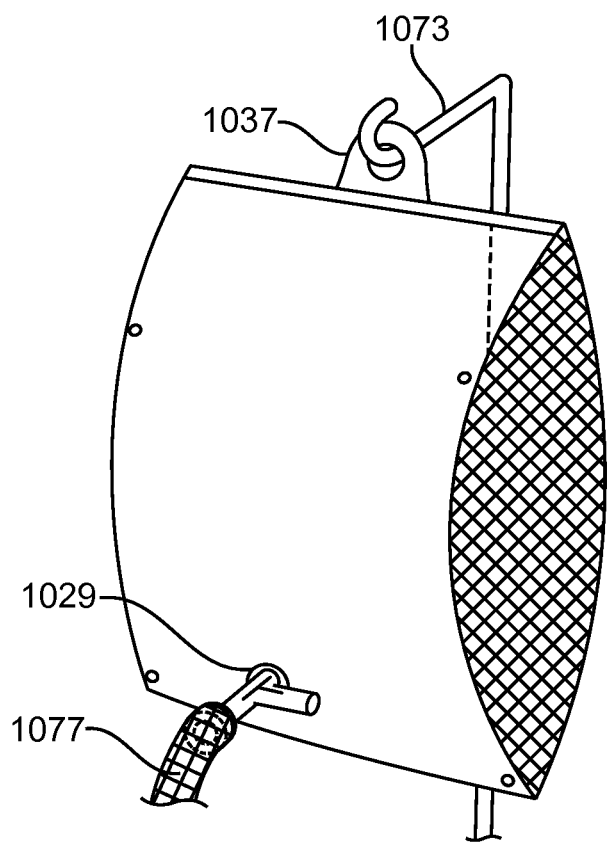

Once the collected stool and solvent is homogenized into a homogenous mixture, the bag 1001 can be hung on an IV pole or other similar apparatus 1073 via hanger tab 1037 as shown in FIG. 10E. Gravity and diffusion can then facilitate the formation of a filtrate that largely comprises the gastrointestinal microflora and other fluids without undesired solids. The filtrate can then be collected via dispenser valve 1029 with a syringe, or tube 1077 that may lead to another collection container, which may itself be an enema or a nasoenterictube leading to a colonoscope or subsequent refinement systems described herein. Dispensation of the filtrate may occur via gravity or with the assistance of a pump or other force. A measured or "metered" dispensing feature may be included as well to ensure the correct amount of microflora is delivered.

Figure 11:
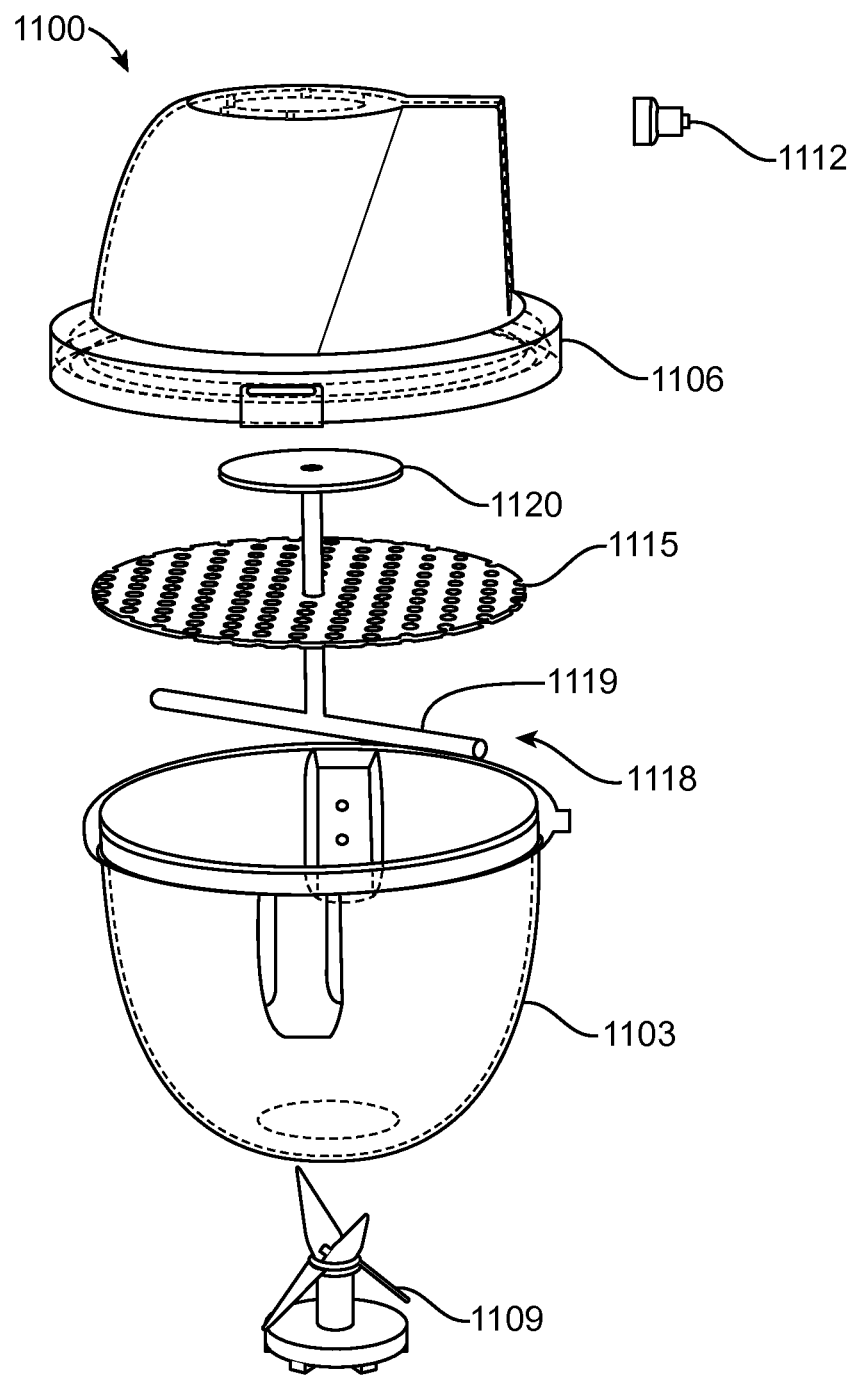
FIG. 11 is an exploded view of a stool collection and filtration container according to an illustrative embodiment, detailing the agitator, main chamber, filter, milling element, collection container and cap, nozzle, and valve.

FIG. 11 is an exploded view of an integrated stool collection and filtration device 1100 according to an embodiment of the invention. The integrated stool collection and filtration system 1100 comprises a stool collection container 1103, a filtrate collection lid 1106, mixing blades 1109, a valve 1112, a filter assembly 1115, and a milling element 1118. The stool collection container 1103 may be used in a similar way to the disposable device 302 described above. Mixing blades 1109 can couple to the stool collection container 1103 at its bottom, and the mixing blades 1109 can be coupled to a base station, such as base station 602 and drive motor 604 described above, to actuate the mixing blades 1109. The stool collection container 1103 may open at the top to collect stool and can interface with a linking mechanism or bracket to the toilet seat as described above. In this manner, the stool collection container 1103 can be separated from the toilet environments. Flexible sheaths may also be used to provide greater protection. Typically, the stool collection container 1103 will be at least partially if not completely opaque to provide a more pleasing aesthetic than if it were transparent.

As shown in FIG. 11, the stool collection container 1103 is in the form of a rigid bowl. In other embodiments, the stool collection container 1103 may be collapsible by having, for example, accordion folds. The stool collection container 1103 may also be in different such as the shape of a common, commercially available blender with vertical ridges to facilitate the increase of turbulent fluid flow when the mixing blades 1109 are spinning.

The filter 1115 can be placed over the stool collection container 1103 to seal the top of the stool collection container 1103. The filter 1115 can comprise one or more, typically two or more, filter sheets to form a "multi-stage" filter as described above. Milling element 1115 transverses the filter 1115 and comprises an arm 1119 to be positioned adjacent the surface of the filter 1115 on the stool collection container side of the device 1100. The opposite end 1120 of the milling element 1115 closes the top of the filtrate collection lid 1106 and can be coupled to a base station much like the mixing blades 1109. Actuating the motor of the base station rotates the arm 1119 of the milling element 1118 to clear the filter 1115. The filtrate collection lid 1106 can be placed over the stool collection container 1103 to close the container 1103. The filtrate collection lid 1106 comprises a valve 1112 from which filtrate can be dispensed, or various substances can be added or removed from the closed system created by the lid. The valve 1112 may be, for example, a 3-way stopcock or a luer valve.

Figure 11A:
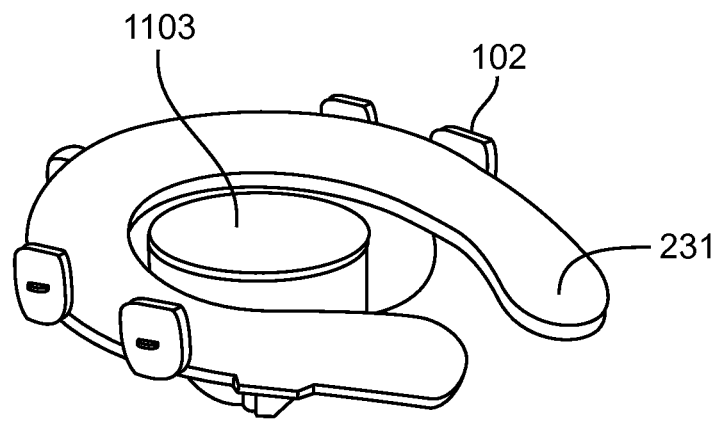
FIGS. 11A to 11E show the stool container of FIG. 11 in use according to the illustrative embodiment.

FIGS. 11A to 11E show the integrated stool collection and filtration device 1100 in use. FIG. 11A shows the stool collection container 1103 coupled to the toilet seat 231 via the bracket 102. A donor can sit on the toilet seat 231 and defecate into the stool collection container 1103. After stool collection, the stool collection container 1103 can be removed from the toilet seat 231 and coupled with the filter 1115, the milling element 1118, and the filtrate collection lid 1106 so that the collected stool is in a closed environment. Suction may be provided through valve 1112 or another valve coupled to either the stool collection container 1103 or the filtrate collection lid 1106 to remove air within the device 1100 to provide an anaerobic environment for the collected stool. Various gases or other substances may also be introduced through the value 1112 to promote an anaerobic environment or viability and growth of microflora contained within. Saline or other sterile solvent can then provided through valve 1112 or another valve coupled to either the stool collection container 1103 or the filtrate collection lid 1106 as described above. Prior to the addition of saline or other sterile solvent, the device 1100 may be weighed to determine the weight of the collected stool and to determine the appropriate volume of saline or other sterile solvent to add based on the measured weight, for example, using the above-described weight-based algorithms.

Figure 11B:
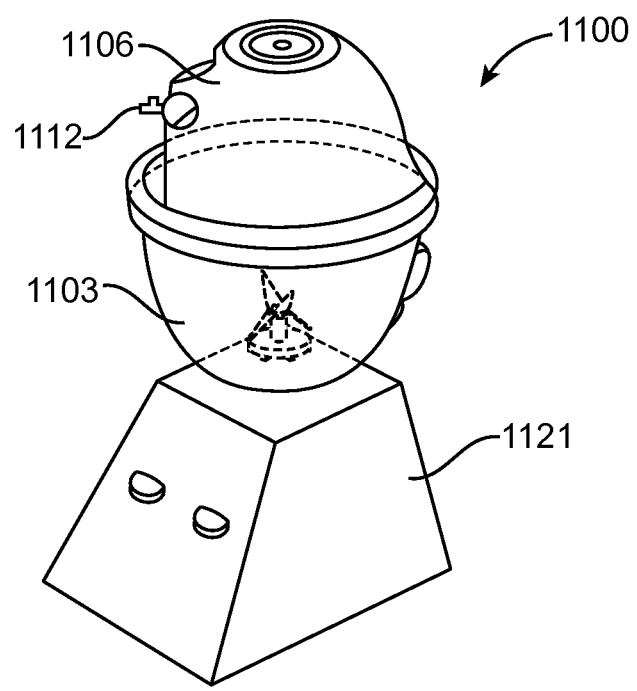

As shown in FIG. 11B, once stool is collected and the device 1100 closed, the device can be coupled to a base station 1121. The base station 1121 will typically be similar to the base stations 602 described above. The base station 1121 has a motor coupled to the mixing blades 1109. This motor actuates the mixing blades 1109 to homogenize the collected stool and the saline or other solvent previously provided to the stool.

Figure 11C:
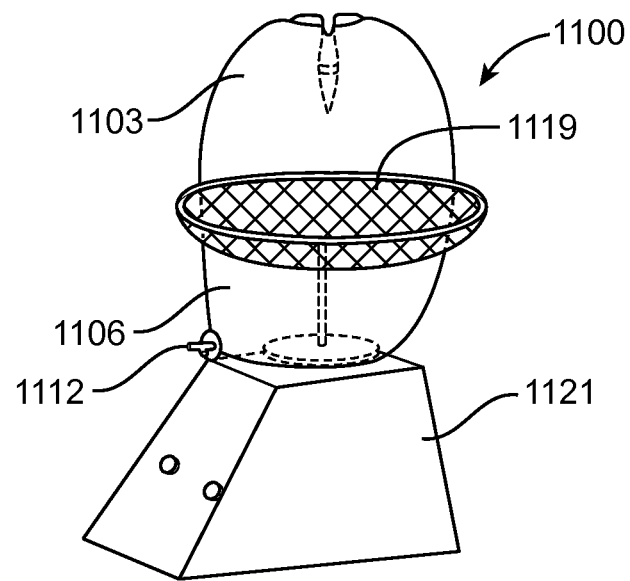

As shown in FIG. 11C, once the stool and solvent is homogenized, the homogenized mixture is filtered. The device 1100 is flipped upside down to couple the top of the device 1100 to the base station 1121. Filtration may be facilitated by gravity and the base station 1121 can actuate the milling arm 1119 to keep the filter 1115 clear as filtration occurs. Filtrate is collected into the filtrate collection lid 1106.

Figure 11D:
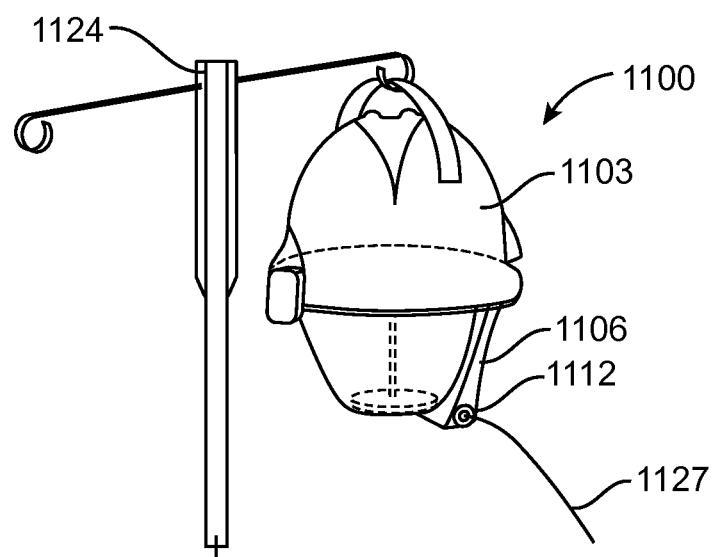
Figure 11E:
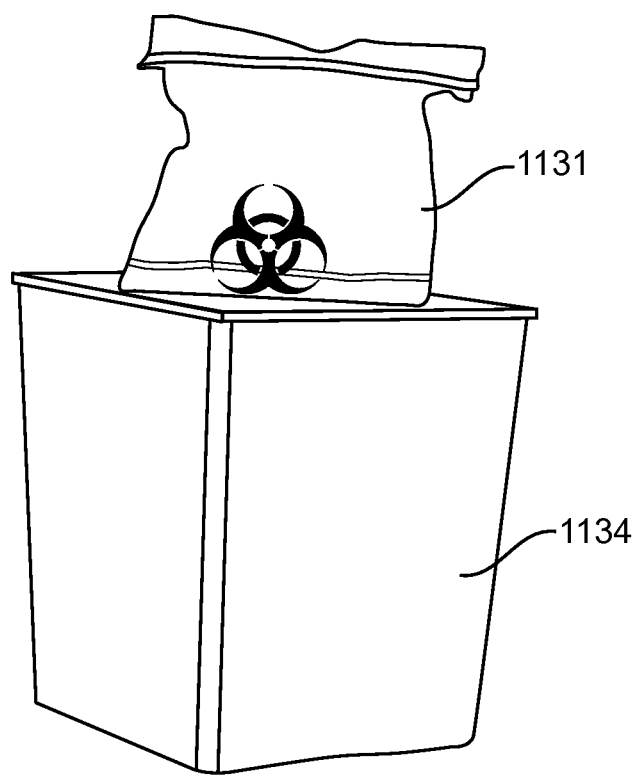

As shown in FIG. 11D, once filtration is complete, the device 1100 is hung upside down, for example, on hanger 1124. Filtrate comprising gastrointestinal microflora but lacking undesired stool solids can be dispensed through the valve 1112 from the filtrate collection lid 1106. The top of the filtrate collection lid 1106 may have a sloped surface to facilitate dispensation of the filtrate when the device 1100 is hung upside down. The valve 1112 can be connected and open to a tubing 1127 to divert the filtrate to any number of other devices including but not limited to an enema tube, a colonoscope, a nasoenteric tube, a syringe, or subsequent refinement systems described herein. Gravity facilitates the dispensation of the filtrate but a pump may be used additionally as well. For example, air may be pumped into the device 1100 through another valve coupled to the device 1100 to force filtrate out through the valve 1112. Once sufficient filtrate is collected, the entire device 1100 can or can not be placed in a bag 1131 and disposed of, for example, into biohazard or trash bin 1134.

Figure 12:
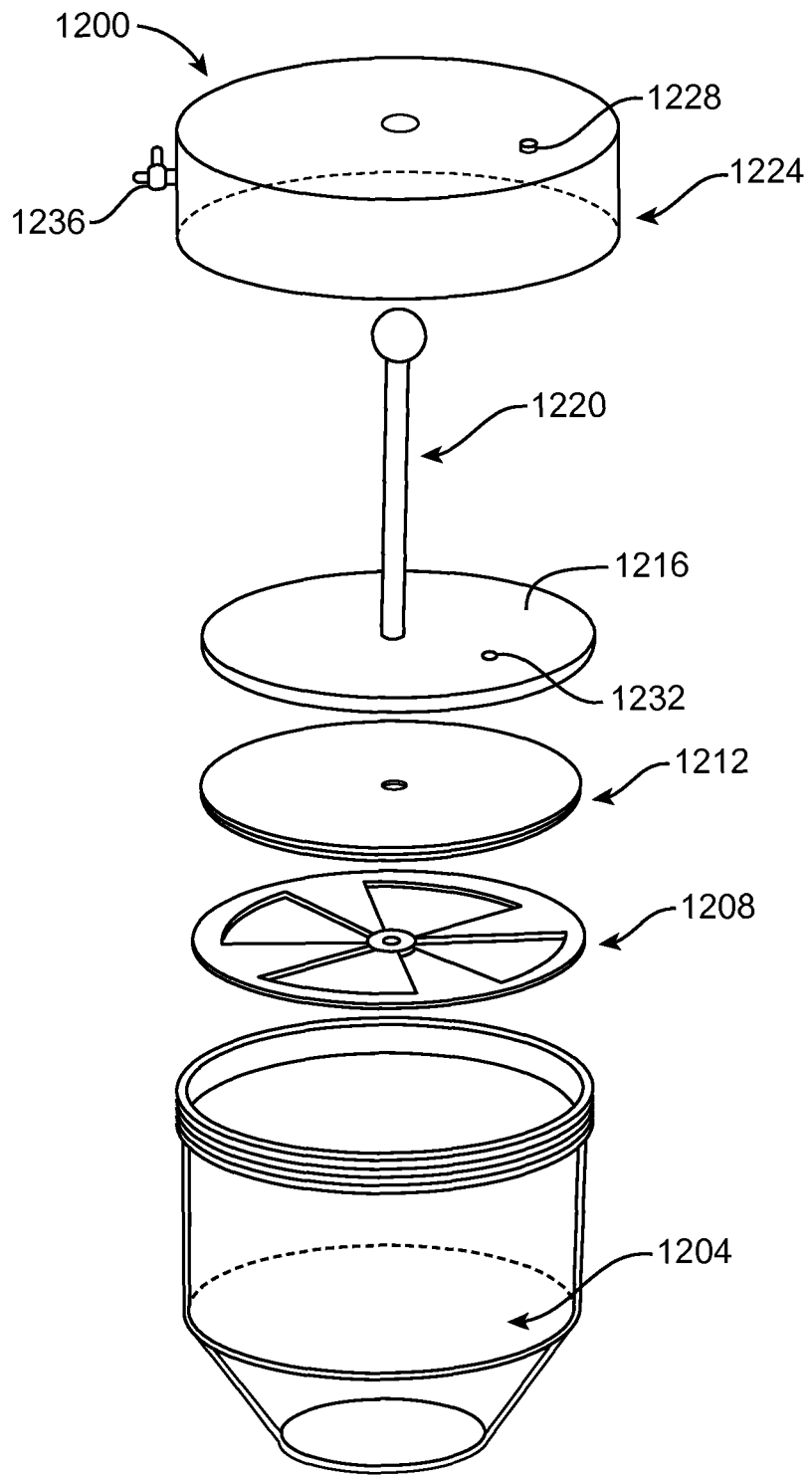
FIG. 12 is an exploded view of a stool collection and filtration container according to an illustrative embodiment.

FIG. 12 is an exploded view of a stool collection and filtration container 1200. The stool collection and filtration container 1200 may be somewhat similar in design to a French press for coffee. The stool collection and filtration container 1200 comprises a stool collection container 1204, a homogenizing plate 1208, a filter 1212, a plunger 1216 comprising a handle 1220 and opening 1232, and a lid 1224 comprising a vent 1228. The stool collection container 1204 will be used similarly to stool collection container 1103 and collects stool as the donor is on the toilet with the assistance of a linking mechanism or bracket. The homogenizing plate 1208 can be driven by the plunger plate 1216 and homogenizes collected stool and added saline or other solvents. The homogenized mixture may be filtered with filter 1212 which may comprise one or more layers of filters to form a "multi-filter" system described above. A vent 1232 in the plunger allows the microflora filtrate to pass into the lid 1224 which caps the stool collection and filtration container 1200. The vent 1228 allows air and other gases to vent out of the container 1200 and may comprise a deodorizing filter such as an activated charcoal filter. The microflora filtrate may also be collected through a valve 1236 in the lid which may be similar to that of the valve 1112 described above.

Figure 13A:
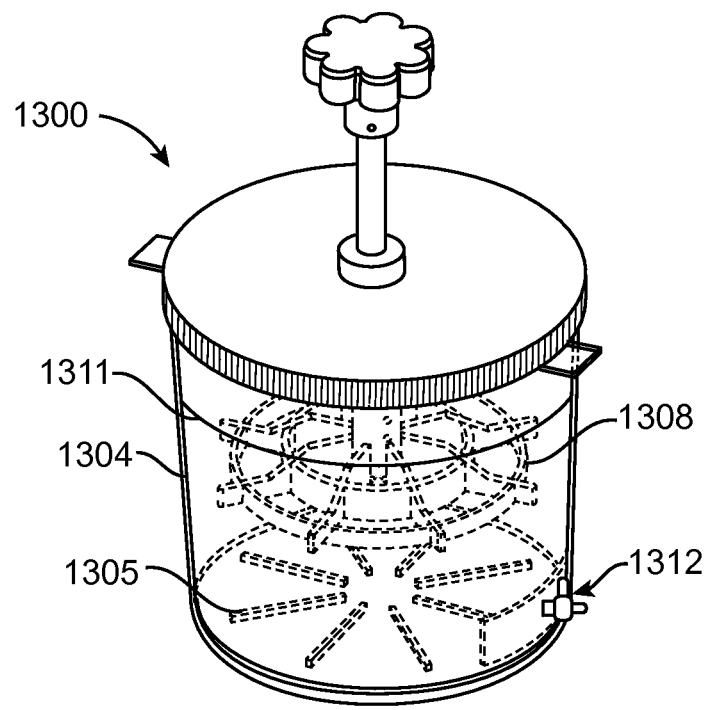
FIGS. 13A and 13B are isometric views of a stool collection and filtration container according to an illustrative embodiment.
Figure 13B:
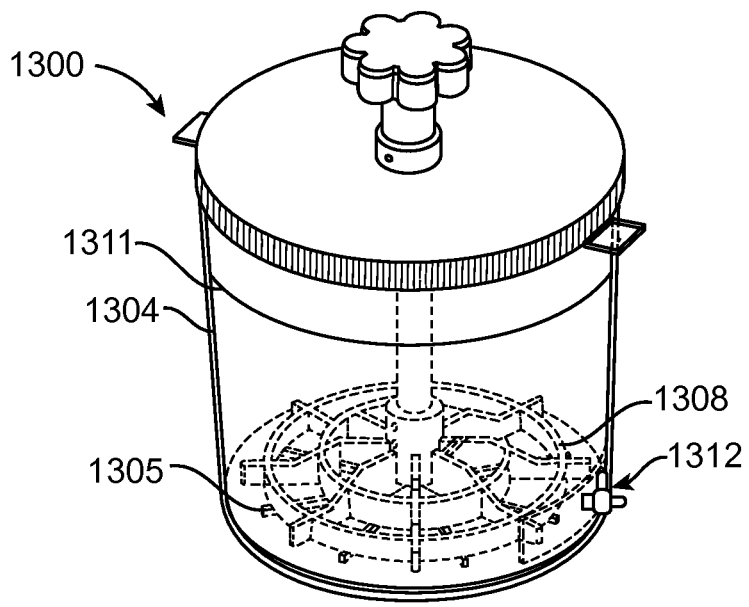

FIGS. 13A and 13B are isometric views of a stool collection and filtration device 1300 having features similar to that of the French press-like device 1200 described above. The container 1300 has additional features such as ridges 1305 on the base of the stool collection container 1305. The homogenizing plate 1308 also comprises multiple, radially disposed arms and multiple, circumferentially disposed rings. The ridges 1305 assist homogenization as they shear against arms and rings of the homogenizing plate 1308 as the homogenizing plate is rotated and plunged down (FIG. 13B). Much like in the device 1200, the device 1300 may comprise a filter plate 1311 on top of the homogenizing plate 1308 that may have a diameter the same as the container 1304 where the plunger seals against the wall of the container. The container may also have an additional filter(s) and a valve 1312 within its wall.

Figure 14:
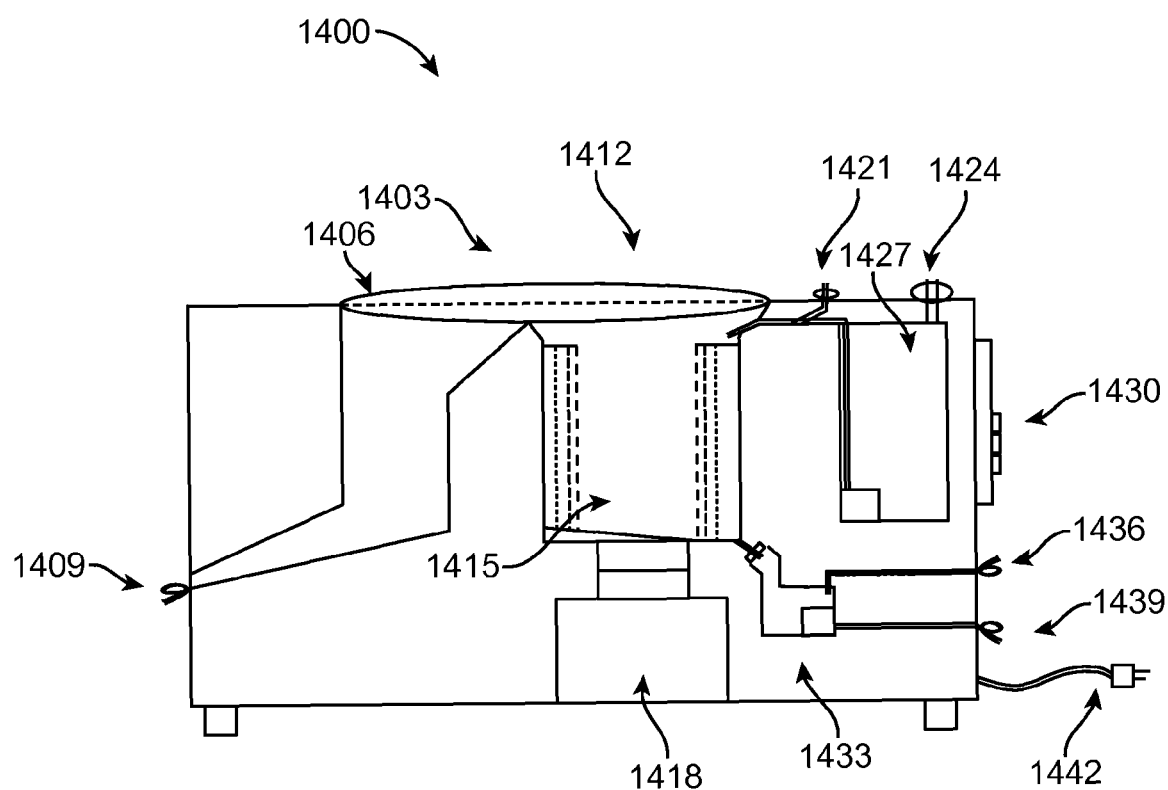
FIG. 14 is a diagram of all-in-one stool collection and filtration toilet system according to an illustrative embodiment.

FIG. 14 is a diagram of an exemplary all-in-one stool collection and filtration toilet system 1400. The toilet system 1400 is a single device that performs all of the stool collection, filtration, filtrate collection, and filtrate dispensation functions described herein without the need to assemble or disassemble any specific features or structural components. The toilet system 1400 comprises a seat and opening 1403. The seat and opening 1403 includes an opening 1406 for urine leading to a port 1409 for the removal of collected urine. The seat and opening 1403 further includes an opening 1412 leading to a container 1415 for the collection and filtration of stool. The openings 1406 and 1412 are typically isolated from each other. The container 1415 may be reusable and may optionally be removed for cleaning or replacement. The container 1415 will typically be adaptable with a filter module, a mixing element, and a base element 1418. The base element 1418 has a similar function to the base station 602 described above and will typically be used to weigh the container 1415 and collected stool as well as actuate any mixing element coupled to the container 1415. The container 1415 can open to a port 1421 for the addition of various constituents if desired and a port 1424 for the addition of saline. The saline port 1424 may be coupled to a saline reservoir and pump 1427 for the introduction of saline or other solvent to the container 1415. The toilet system 1400 further includes a control panel 1430 for the control of the base 1418, the saline reservoir and pump 1427, as well as the filtrate collection chamber and pump 1433. The filtrate collection chamber and pump 1433 collects filtrate from the container 1415 from an exit port in the bottom of the container 1415. The container 1415 may have a sloped bottom to facilitate the exit of the filtrate from that exit port to the filtrate collection chamber and pump 1433. The filtrate can be pumped out by the filtrate collection and pump 1433 through port 1439. Prior to the dispensation of the filtrate, other constituents, for example deodorizing agents, may be added to the filtrate through port 1436. The port 1439 may provide filtrate to any number of other containers and devices as described above. Power is provided to the toilet system 1400 through power cord 1442.

Figure 15A:
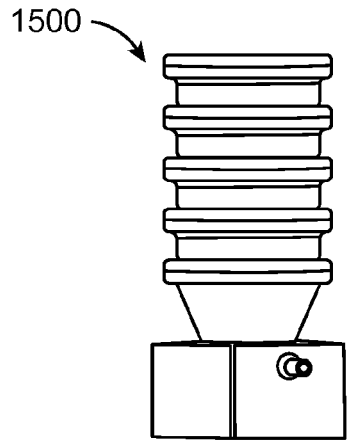
FIGS. 15A to 15E show a filtrate refinement system according to an illustrative embodiment.
Figure 15B:
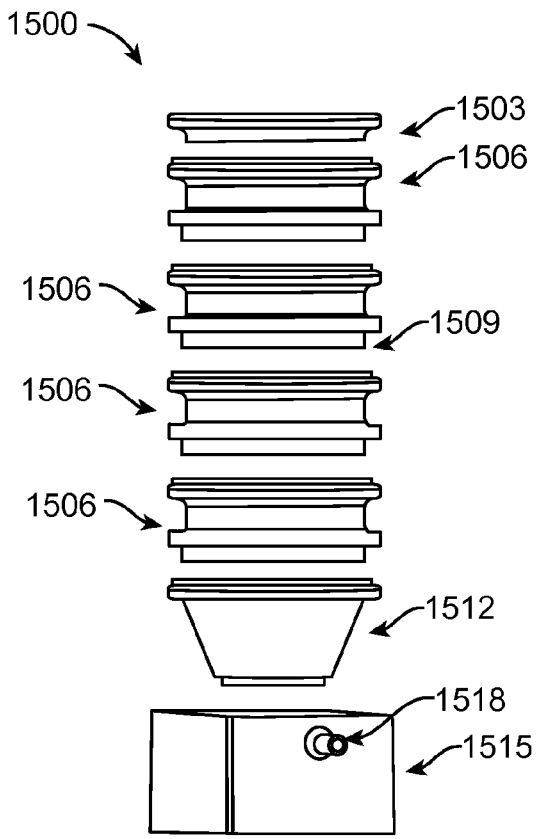
Figure 15C:
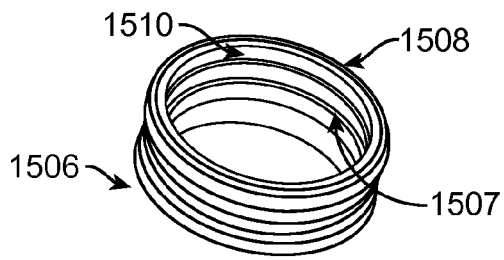
Figure 15D:
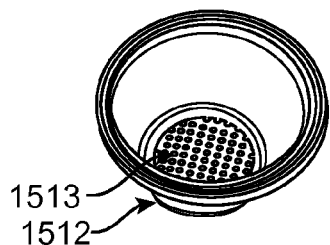
Figure 15E:
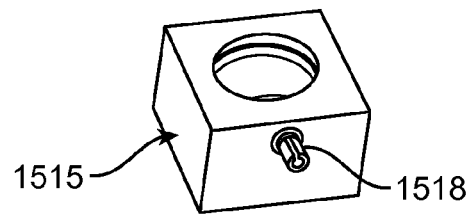

As discussed above with reference to FIGS. 9A to 9D, subsequent components or apparatuses may be provided to facilitate further refinement, processing, isolation, or analysis of the filtrate and its contents for subsequent use in a wide variety of applications. Various filtrate refinement systems for the refinement of microflora are further provided by the present invention. FIGS. 15A to 15E show a filtrate refinement system 1500. FIG. 15A shows the filtrate refinement system 1500 in an assembled form while FIG. 15B shows an exploded view of the filtrate refinement system 1500 with its component sections. The filtrate refinement system 1500 comprises a lid 1503, several screen filter segments 1506, a final collection chamber 1512, and a vacuum chamber 1515, which are all coupled to each other via threads such as threads 1509 on the underside of the screen filters 1506. The several screen filter segments 1506 may each have different filter pore sizes and they may be arranged in descending order of filter pore sizes. The lid 1503 may have a connector to an upstream device such as any of the filtrate dispensation ports described above and filtrate may be dispensed into the filtrate refinement system 1500 in a measured manner. FIG. 15C shows a closer view of a screen filter 1506, which comprises a screen insertion point 1507, a thread insertion point 1510 for the insertion of threads 1509 on an adjacent screen filter 1506, and a notch 1508 for a rubber seal which will typically be a raised structure on top of the parts of the filtrate refinement system 1500 and an indented structure of the bottom of the parts. Methods may be provided to agitate the screen filters 1506 to facilitate passage of the filtrate through the filters. FIG. 15D shows a closer view of the final collection chamber 1512. At the bottom of final collection chamber 1512 is a biological filter, for example a 0.45 µm or smaller biological filter, that may allow liquids, biological molecules, and larger non-biological particles to pass through while retaining much of the gastrointestinal microflora in the collection chamber 1512. In some cases, the final collection container 1512 may be connected to a centrifuge for further refinement of the collected microflora, or may be connected to other containers such as those described above in FIGS. 9A-9D. FIG. 15E shows a closer view of the vacuum chamber 1515 including vacuum port 1518.

FIGS. 16A to 16C show a filtrate refinement system 1600 according to an alternate embodiment. The filtrate refinement system 1600 is similar in many respects to the filtrate refinement system 1500. As shown in FIG. 16A, the filtrate refinement system 1600 comprises a lid 1603, a series of screen filters 1606a, 1606b, 1606c, 1606d, and a fluid collection section 1612 which are stackable and separable from each other. The interior of the screen filters 1606a, 1606b, 1606c, and 1606d comprise agitation bars 1609a, 1609b, 1609c, and 1609d, respectively. As shown in FIGS. 16B and 16C, the filtrate refinement system 1600 may be adaptable to a blender base 1615 which may rotate one or more of the screen filters 1606a, 1606b, 1606c, and 1606d while the non-rotated screen filters remain stationary. The blender base 1615 comprises a captor frame 1618 into which the refinement system 1600 is placed. The captor frame 1618 comprises a top portion 1618T to restrict vertical movement of the refinement system 1600. The captor frame 1618 comprises one or more gear drives 1621 which couple to and can rotate an individual screen filter. As clearly shown in FIG. 16B, screen filters 1606a and 1606c are coupled with gear drives 1621. The captor frame 1618 further comprises slide locks 1624 which couple to and hold stationary an individual screen filter. As clearly shown in FIG. 16C, screen filters 1606b and 1606d and fluid collection section 1612 are held stationary by slide locks 1624. The blender base 1615 comprises a rotating driver 1633 which rotates shaft 1627 which in turn rotates gear drives 1621 to agitate selected screen filters. The top 1618T of the captor frame 1618 comprises a bearing 1630 to accommodate the top of the shaft 1627.

Figure 17A:
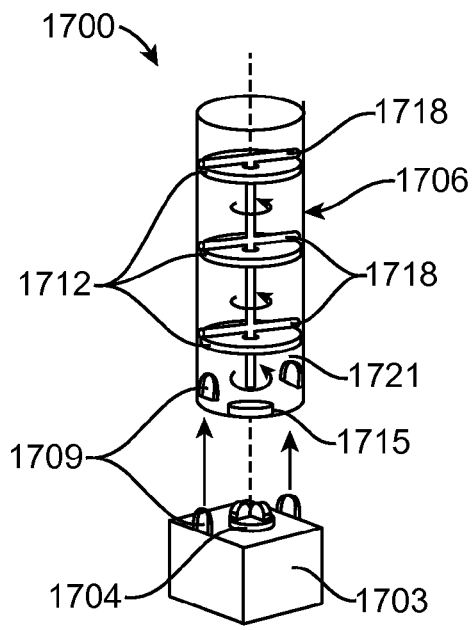
FIGS. 17A and 17B show a filtrate refinement system according to another alternate embodiment.
Figure 17B:
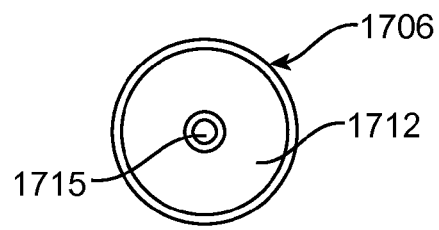

FIGS. 17A and 17B show a filtrate refinement system 1700 according to another alternate embodiment. FIG. 17A shows an exploded view of the filtrate refinement system 1700 and FIG. 17B shows a cross-section of the system 1700 taken along a filter 1706. The filtrate refinement system 1700 comprises a motor base 1703 and a filter assembly 1706 that couples to the motor base 1703 via slide locks 1709. The filter assembly 1706 comprises a series of filters 1712 each having an opening at its center to accommodate shaft assembly 1715. The shaft assembly 1715 can be coupled to the motor base 1703 through motor 1714. The shaft assembly 1715 comprises milling arms 1718 each positioned adjacent a filter 1712. The milling arms 1718 rotate to clear the filter 1712. The bottom of the filter assembly 1706 comprises a filtrate collection chamber 1715.

Figure 18A:
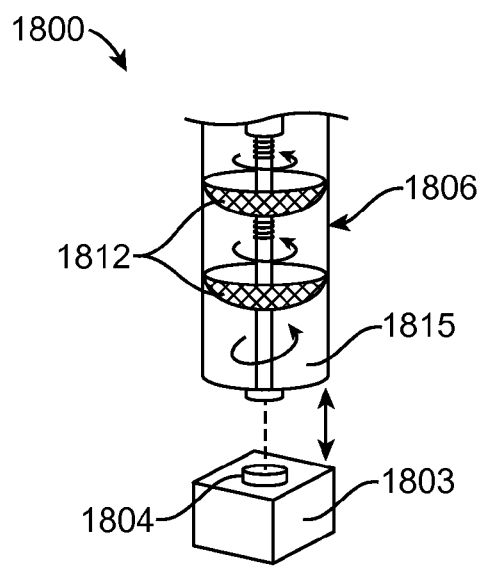
FIGS. 18A and 18B show a filtrate refinement system according to yet another alternate embodiment.
Figure 18B:
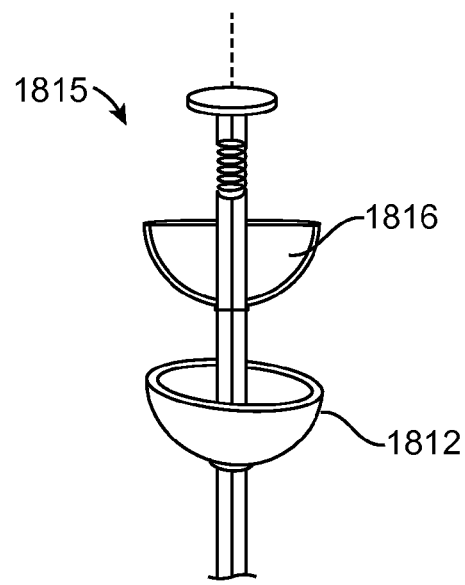

FIGS. 18A and 18B show a filtrate refinement system 1800 according to yet another alternate embodiment. The filtrate refinement system 1800 is similar to the filtrate refinement system 1700 described above. The filtrate refinement system 1800 comprises a motor base 1803 having a motor 1804 that can couple to shaft assembly 1815 of the filter assembly 1806. As shown in FIGS. 18A and 18B, the filters 1812 are rounded and the milling arms 1816 are rounded and act as agitator blades which may be pushed down with spring-loaded shaft assembly 1815.

Figures 19A, 19B:
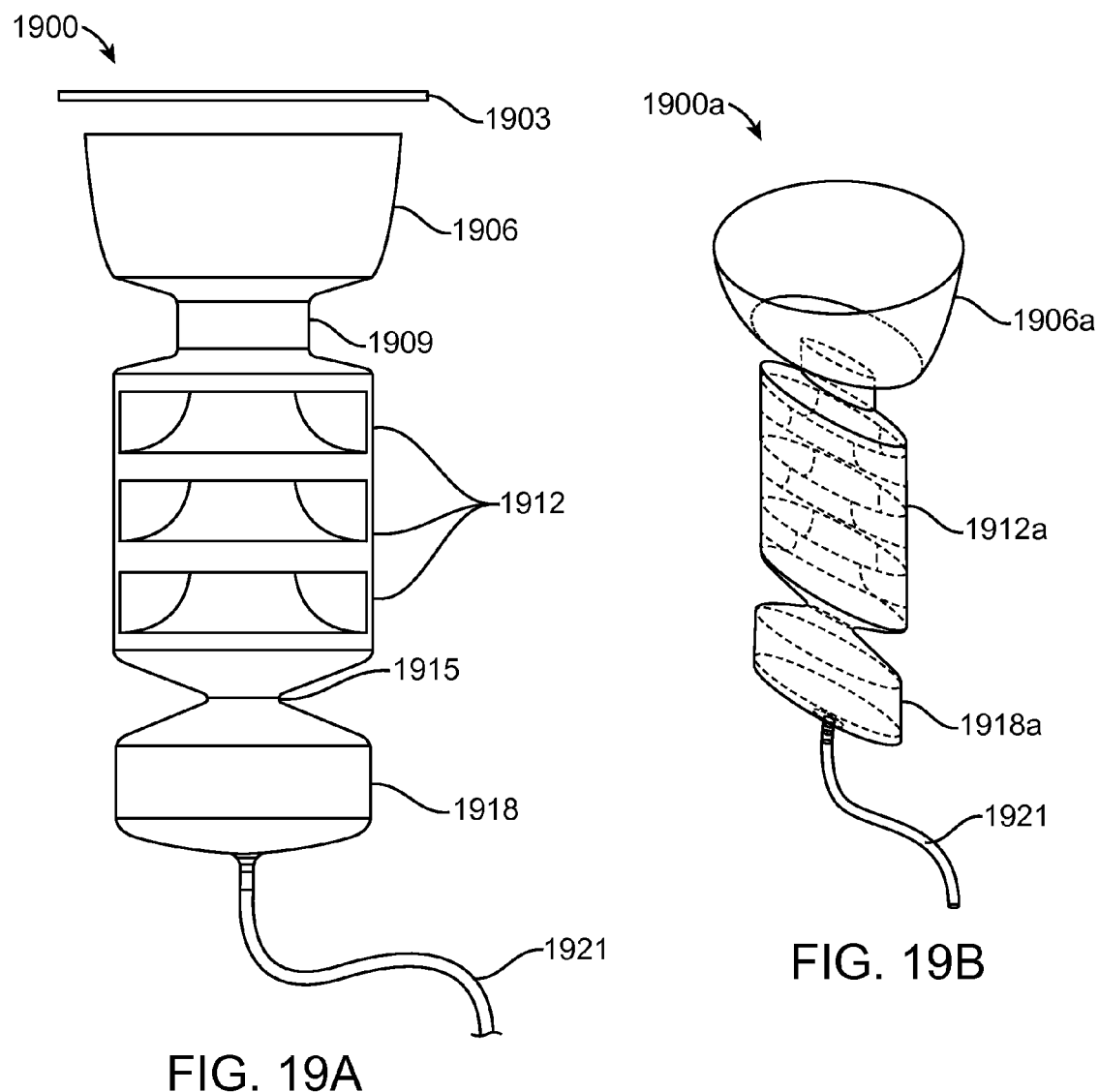
FIGS. 19A and 19B show a filtrate refinement system according to a further alternate embodiment.

FIGS. 19A and 19B show a filtrate refinement systems 1900 and 1900a according to a further alternate embodiment. The filtrate refinement system 1900 can be used to collect stool, filter a mixture of stool and saline or other solvent, and refine the microflora filtrate in a single device. The top of the filtrate refinement system 1900 can be capped off and sealed with a closure system 1903. Stool can be collected with the receptacle 1906 wherein saline or other solvent can be added and homogenized with the collected stool. The receptacle 1906 can lead into the sequential filter sections 1912 which form a "multi filter" system much like that described above. Between the sequential filter system 1912 and the receptacle 1906 is a first sealable stage 1909 which can be opened and closed to regulate the flow of liquid from the receptacle 1906 to the sequential filter sections 1912. Likewise, a second sealable stage 1915 may be disposed between the filtrate collection reservoir 1918 and the sequential filter sections 1912. Filtrate can be collected from the filtrate collection reservoir 1918 with delivery tube 1921. The filtrate refinement system 1900*a* shown in FIG. 19B is similar to the filtrate refinement system 1900 except that the bottoms of the receptacle 1906*a*, the sequential filter sections 1912*a*, and the collection reservoir 1918*a* are sloped to facilitate the downward flow of liquid through the filtrate refinement system 1900*a*.

In addition to the other components described above, the ability to isolate and store microflora or other contained contents through centrifugation can be desirable to optimize a wide variety of applications including, but not limited to therapeutic, diagnostic and analytic uses (as set forth above).

Accordingly, this description is meant to be taken only by way of example, and not to otherwise limit the scope of this invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of isolating gastrointestinal microflora from stools of a donor, the method comprising:
   providing a toilet bracket which is removably coupled to a toilet seat such that the toilet bracket is centered at an opening of the toilet seat;
   providing a container for collecting stool, wherein the container is coupled to the toilet bracket to be centered at the opening of the toilet seat;
   collecting stool from the donor in the container as the donor is defecating while seated on the toilet seat,
   wherein the container is sealed after the stool is collected to place the collected stool in a closed environment;
   introducing a solvent through an introduction port into the sealed container;
   homogenizing the solvent and collected stool within the sealed container to form a mixture; and
   filtering the homogenized mixture to extract a filtrate comprising the solvent and gastrointestinal microflora from the mixture within the sealed container, the filtrate having reduced solids.

2. The method of claim 1, further comprising dispensing the filtrate from a dispenser port in the container.

3. The method of claim 2, wherein the introduction port and the dispenser port are the same.

4. The method of claim 1, wherein the closed environment is anaerobic.

5. The method of claim 1, wherein the container is closed to toilet water while stool is collected.

6. The method of claim 1, wherein the container is configured to accommodate a variable volume of stool and solvent.

7. The method of claim 1, wherein the container is at least partially made of an expandable material.

8. The method of claim 1, wherein the container is collapsible.

9. The method of claim 1, wherein the container is at least partially opaque.

10. The method of claim 1, wherein the container comprises a vent having a deodorizing filter.

11. The method of claim 1, wherein sealing the container comprises closing an opening in the container from which stool is collected and applying a negative pressure through a suction port in the container to remove air from the container.

12. The method of claim 11, wherein the filtrate is collected from a dispensing port of the sealed container, and wherein the suction port is the same as at least one of the introduction port or dispensing port.

13. The method of claim 1, wherein the solvent comprises one of saline, milk, or other sterile buffer.

14. The method of claim 1, wherein the volume of solvent introduced results in the homogenized mixture being of a predetermined density.

15. The method of claim 1, further comprising weighing the container and determining the weight of the collected stool, and wherein the volume of solvent introduced depends on the determined weight of the collected stool.

16. The method of claim 1, wherein homogenizing the solvent and collected stool comprises applying external physical force to the container.

17. The method of claim 16, wherein the container comprises a flexible bag and homogenizing the solvent and collected stool comprises placing the flexible bag in at least one of a roller mechanism, a mashing mechanism, or paddle blender.

18. The method of claim 1, wherein homogenizing the solvent and collected stool comprises actuating a mixer within the container.

19. The method of claim 1, wherein filtering the homogenized mixture comprises passing the homogenized mixture through at least two filters.

20. The method of claim 19, wherein passing the homogenized mixture through at least two filters comprises passing the homogenized mixture through a first filter and passing the homogenized mixture through a second filter having a pore size smaller than the first filter.

21. The method of claim 20, wherein the first filter has a pore size of at most 4,000 µm.

22. The method of claim 20, wherein the second filter has a pore size of at least 0.22 µm.

23. The method of claim 1, wherein filtering the homogenized mixture comprises pressing the homogenized mixture against a filter.

24. The method of claim 23, wherein the filter has a pore size in the range of 0.22 µm to 4,000 µm.

25. A method of isolating gastrointestinal microflora from stools of a donor, the method comprising:
   providing a toilet bracket which is removably coupled to a toilet seat such that the toilet bracket is centered at an opening of the toilet seat;
   providing a container for collecting stool, wherein the container is coupled to the toilet bracket to be centered at the opening of the toilet seat;
   collecting stool from the donor in a container as the donor is defecating while seated on the toilet seat,
   wherein the container is sealed after the stool is collected to place the collected stool in a closed environment;
   introducing a solvent through an introduction port into the sealed container;
   homogenizing the solvent and collected stool within the sealed container to form a mixture;
   filtering the homogenized mixture to extract a filtrate comprising the solvent and gastrointestinal microflora from the mixture within the sealed container, the filtrate having reduced solids; and
   weighing the container and determining the weight of the collected stool, and wherein the volume of solvent introduced depends on the determined weight of the collected stool, wherein the filtrate is collected from a dispensing port of the sealed container, and wherein the suction port is the same as at least one of the introduction port or dispensing port.

26. The method of claim 25, further comprising dispensing the filtrate from a dispenser port in the container.

27. The method of claim 26, wherein the introduction port and the dispenser port are the same.

28. The method of claim 26, wherein the closed environment is anaerobic.

29. The method of claim 25, wherein the container is closed to toilet water while stool is collected.

30. The method of claim 25, further comprising providing a linking mechanism coupling a toilet seat for the donor to the container for collecting stool.

31. The method of claim 25, wherein the container is configured to accommodate a variable volume of stool and solvent.

32. The method of claim 25, wherein the container is at least partially made of an expandable material.

33. The method of claim 25, wherein the container is collapsible.

34. The method of claim 25, wherein the container is at least partially opaque.

35. The method of claim 25, wherein the container comprises a vent having a deodorizing filter.

36. The method of claim 25, wherein sealing the container comprises closing an opening in the container from which stool is collected and applying a negative pressure through a suction port in the container to remove air from the container.

37. The method of claim 25, wherein the solvent comprises one of saline, milk, or other sterile buffer.

38. The method of claim 25, wherein the volume of solvent introduced results in the homogenized mixture being of a predetermined density.

39. The method of claim 25, wherein homogenizing the solvent and collected stool comprises applying external physical force to the container.

40. The method of claim 39, wherein the container comprises a flexible bag and homogenizing the solvent and collected stool comprises placing the flexible bag in at least one of a roller mechanism, a mashing mechanism, or paddle blender.

41. The method of claim 25, wherein homogenizing the solvent and collected stool comprises actuating a mixer within the container.

42. The method of claim 25, wherein filtering the homogenized mixture comprises pressing the homogenized mixture against a filter.

43. The method of claim 42, wherein the filter has a pore size in the range of 0.22 µm to 4,000 µm.

44. The method of claim 25, wherein the toilet bracket comprises a plurality of arms for removably securing the toilet bracket to the toilet seat.

45. The method of claim 1, wherein the toilet bracket comprises a plurality of arms for removably securing the toilet bracket to the toilet seat.

* * * * *